US007037913B2

(12) United States Patent
Wang et al.

(10) Patent No.: US 7,037,913 B2
(45) Date of Patent: May 2, 2006

(54) BICYCLO 4.4.0 ANTIVIRAL DERIVATIVES

(75) Inventors: Tao Wang, Middletown, CT (US); Owen B. Wallace, Zionsville, IN (US); Nicholas A. Meanwell, East Hampton, CT (US); John F. Kadow, Wallingford, CT (US); Zhongxing Zhang, Madison, CT (US); Zhong Yang, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 124 days.

(21) Appl. No.: 10/393,030

(22) Filed: Mar. 20, 2003

(65) Prior Publication Data
US 2004/0009985 A1    Jan. 15, 2004

Related U.S. Application Data

(60) Provisional application No. 60/376,731, filed on May 1, 2002.

(51) Int. Cl.
*A61K 31/497* (2006.01)
*C07D 401/00* (2006.01)

(52) U.S. Cl. .......................... 514/253.05; 514/253.06; 544/363

(58) Field of Classification Search ................ 544/363; 514/253.05, 253.06
See application file for complete search history.

(56) References Cited

U.S. PATENT DOCUMENTS

| | | | | | |
|---|---|---|---|---|---|
| 3,277,085 | A | * | 10/1966 | Aebi et al. ................ | 260/247.2 |
| 4,374,990 | A | * | 2/1983 | Weber et al. ................ | 544/376 |
| 4,791,104 | A | | 12/1988 | Picciola et al. ................ | 514/58 |
| 5,023,265 | A | | 6/1991 | Scherlock et al. .......... | 514/300 |
| 5,124,327 | A | | 6/1992 | Greenlee et al. .......... | 514/235.2 |
| 5,424,329 | A | | 6/1995 | Boschelli et al. ........... | 514/418 |
| 5,736,539 | A | * | 4/1998 | Graham ....................... | 514/218 |
| 6,172,085 | B1 | | 1/2001 | Ohkawa et al. ............. | 514/320 |
| 6,573,262 | B1 | * | 6/2003 | Wallace et al. ........... | 514/235.2 |

FOREIGN PATENT DOCUMENTS

| | | | |
|---|---|---|---|
| CA | 2342251 | * | 3/2000 |
| EP | 0530907 A1 | | 3/1993 |
| WO | WO 93/01181 | | 1/1993 |
| WO | WO 95/04742 | | 2/1995 |
| WO | WO 96/11929 | | 4/1996 |
| WO | WO 97/28141 | | 8/1997 |
| WO | WO 00/12074 | | 3/2000 |
| WO | WO 00/51984 | | 9/2000 |

OTHER PUBLICATIONS

Burckhalter et al, "Antiamebic Agents. V. Promising Basic Amebicides Derived from 5-Chloro-8-Quinolinol" Journal of Organi Chemistry, vol. 26, pp. 4070-4078 (1961).*

Ghosh and Basu, "Chemotherapy of Filariasis: Part I—Some Isoquinolypiperazine Derivatives" Indian Journal of Chemistry, vo 1(12), pp. 528-529 (1963).*

(Continued)

*Primary Examiner*—James O. Wilson
*Assistant Examiner*—Zachary C. Tucker
(74) *Attorney, Agent, or Firm*—Samuel J. DuBoff

(57) ABSTRACT

This invention provides compounds of Formula I having drug and bio-affecting properties, their pharmaceutical compositions and method of use. In particular, the invention is concerned with amido piperazine derivatives. These compounds possess unique antiviral activity, whether used alone or in combination with other antivirals, antiinfectives, immunomodulators or HIV entry inhibitors. More particularly, the present invention relates to the treatment of HIV and AIDS.

I

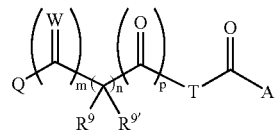

wherein:
Q is

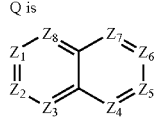

A is selected from the group consisting of $C_{1-6}$alkoxy, $C_{1-6}$alkyl, $C_{3-7}$cycloalkyl, phenyl, and heteroaryl; wherein said heteroaryl may be monocyclic or bicyclic and may be comprised of three to eleven atoms selected from the group consisting of C, N, $NR^9$, O, and S, and wherein each ring of said phenyl and heteroaryl is optionally substituted with one to five same or different substituents selected from the group consisting of $R^{19}$–$R^{23}$;

W is O or —NH;

T is

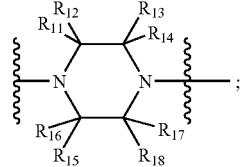

$Z^1$ is $CR^1$ or N;

$Z^2$ is $CR^2$ or N;

$Z^3$ is $CR^3$ or N;

$Z^4$ is $CR^4$ or N;

$Z^5$ is $CR^5$ or N;

$Z^6$ is $CR^6$ or N;

$Z^7$ is $CR^7$ or N;

$Z^8$ is $CR^8$ or N.

6 Claims, No Drawings

OTHER PUBLICATIONS

El-Sebia'a et al, "Synthesis of Some Quinoline Derivatives of Potential Antiamebic Activity" Pharmazie, vol. 32(3), pp. 155-156 (1977).*

H. C. Koppel, et al, "Synthetic Approaches to Quinoxaline Antibiotics. Synthesis of Bisquinoxaloyl Derivatives," J. Org. Chem., vol. 28, pp. 1119-1122, 1963.

M. Font, et al, "Indoles and Pyridazino[4,5-b]Indoles as Nonnucleoside Analog Inhibitors of HIV-1 Reverse Transcriptase," Eur. J. Med. Chem., 30, pp. 963-971, 1995.

D. L. Romero, et al., J. Med. Chem., 36, pp. 1505-1508, 1993.

S. D. Young, et al, "2-Heterocyclic Indole-3-Sulfones as Inhibitors of HIV-1 Reverse Transcriptase," Bioorganic & Medicinal Chemistry Letters, 5(5), pp. 491-496, 1995.

M. J. Genin, et al, "Synthesis and Bioactivity of Novel Bis(Heteroaryl)Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.

R. Silvestri, et al, Antiviral Chemistry & Chemotherapy, 9, pp. 139-148, 1998.

A. Fredenhagen, et al, "Semicochliodinol A and B: Inhibitors of HIV-1 Protease and EGF-R Protein Tyrosine Kinase Related to Asterriquinones Produced by the Fungus *Chrysosporium Merdarium*," Journal of Antibiotics, 50(5), pp. 395-401, 1997.

M. Kato, et al, "New 5-$HT_3$ (Serotonin-3) Receptor Antagonists. IV. Synthesis and Structure-Activity Relationships of Azabicycloalkaneacetamide Derivatives," Chem. Pharm. Bull., 43(8), pp. 1351-1357, 1995.

V. Levacher, et al, "Broadening in the Scope of NADH Models by Using Chiral and Non-Chiral Pyrrolo [2,3-b] Pyridine Derivatives," TETRAHEDRON, 47(3), pp. 429-440, 1991.

Nicolau, K.C., et al, "A Novel Strategy for the Solid-Phase Synthesis of Substituted Indolines," J. AM. Chem. Soc., 122(12), pp. 2966-2967, 2000.

* cited by examiner

BICYCLO 4.4.0 ANTIVIRAL DERIVATIVES

REFERENCE TO RELATED APPLICATIONS

This application claims the benefit of U.S. Provisional Application Ser. No. 60/376,731 filed May 1, 2002.

FIELD OF THE INVENTION

This invention provides compounds having drug and bio-affecting properties, their pharmaceutical compositions and method of use. In particular, the invention is concerned with new heterocyclic amidopiperazine derivatives that possess unique antiviral activity. More particularly, the present invention relates to compounds useful for the treatment of HIV and AIDS.

BACKGROUND ART

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains –3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and seven peptidomimetic protease inhibitors or approved formulations: saquinavir, indinavir, ritonavir, nelfinavir, amprenavir, lopinavir, and Kaletra® (lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6–14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: perspectives on novel therapeutic compounds and strategies for the treatment of HIV infection. has appeared (Buckheit, Robert W., Jr. Expert Opinion on Investigational Drugs 2001, 10(8), 1423–1442). A review covering both NRTI and NNRTIs has appeared (Balzarini, J.; De Clercq, E. Antiretroviral Therapy 2001, 31–62.). An overview of the current state of the HIV drugs has been published (E. De clercq Journal of Clinical Virology, 2001, 22, 73–89).

Several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). Finally, 3-substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23; Levacher et al, Ref. 24; Dompe Spa, WO-09504742, Ref. 5(a); SmithKline Beecham PLC, WO-09611929, Ref. 5(b); Schering Corp., U.S. Pat. No. 5,023,265, Ref. 5(c)). However, these structures differ from those claimed herein in that they are aza-indole mono-amide rather than unsymmetrical aza-indole piperazine diamide derivatives, and there is no mention of the use of these compounds for treating viral infections, particularly HIV. Nothing in these references can be construed to disclose or suggest the novel compounds of this invention and their use to inhibit HIV infection.

REFERENCES CITED

Patent Documents
1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.;

Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications

6. Larder, B. A.; Kemp, S. D. Multiple mutations in the HIV-1 reverse transcriptase confer high-level resistance to zidovudine (AZT). *Science,* 1989, 246,1155–1158.
7. Gulick, R. M. Current antiretroviral therapy: An overview. *Quality of Life Research,* 1997, 6, 471–474.
8. Kuritzkes, D. R. HIV resistance to current therapies. *Antiviral Therapy,* 1997, 2 (Supplement 3), 61–67.
9. Morris-Jones, S.; Moyle, G.; Easterbrook, P. J. Antiretroviral therapies in HIV-1 infection. *Expert Opinion on Investigational Drugs,* 1997, 6(8),1049–1061.
10. Schinazi, R. F.; Larder, B. A.; Mellors, J. W. Mutations in retroviral genes associated with drug resistance. *International Antiviral News,* 1997, 5,129–142,.
11. Vacca, J. P.; Condra, J. H. Clinically effective HIV-1 protease inhibitors. *Drug Discovery Today,* 1997, 2, 261–272.
12. Flexner, D. HIV-protease inhibitors. *Drug Therapy,* 1998, 338, 1281–1292.
13. Berkhout, B. HIV-1 evolution under pressure of protease inhibitors: Climbing the stairs of viral fitness. *J. Biomed. Sci.,* 1999, 6, 298–305.
14. Ren, S.; Lien, E. J. Development of HIV protease inhibitors: A survey. *Prog. Drug Res.,* 1998, 51, 1–31.
15. Pedersen, O. S.; Pedersen, E. B. Non-nucleoside reverse transcriptase inhibitors: the NNRTI boom. *Antiviral Chem. Chemother.* 1999, 10, 285–314.
16. (a) De Clercq, E. The role of non-nucleoside reverse transcriptase inhibitors (NNRTIs) in the therapy of HIV-1 infection. *Antiviral Research,* 1998, 38, 153–179. (b) De Clercq, E. Perspectives of non-nucleoside reverse transcriptase inhibitors (NNRTIs) in the therapy of HIV infection. IL. *Farmaco,* 1999, 54, 26–45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino[4,5-b]indoles as nonnucleoside analog inhibitors of HIV-1 reverse transcriptase. *Eur. J. Med. Chem.,* 1995, 30, 963–971.
18. Romero, D. L.; Morge, R. A.; Genin, M. J.; Biles, C.; Busso, M,; Resnick, L.; Althaus, I. W.; Reusser, F.; Thomas, R. C and Tarpley, W. G. Bis(heteroaryl)piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.,* 1993, 36, 1505–1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.,* 1995, 5, 491–496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.,* 1996, 39, 5267–5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139–148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium. Antibiotics,* 1997, 50, 395–401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.,* 1995, 43, 1351–1357.
24. Levacher, V.; Benoit, R.; Duflos, J; Dupas, G.; Bourguignon, J.; Queguiner, G. Broadening the scope of NADH models by using chiral and non chiral pyrrolo [2,3-b] pyridine derivatives. *Tetrahedron,* 1991, 47, 429–440.
25. Shadrina, L. P.; Dormidontov, Yu. P.; Ponomarev, V, G.; Lapkin, I. I. Reactions of organomagnesium derivatives of 7-aza- and benzoindoles with diethyl oxalate and the reactivity of ethoxalylindoles. *Khim. Geterotsikl. Soedin.,* 1987, 1206–1209.
26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100–106.
27. (a) Desai, M.; Watthey, J. W. H.; Zuckerman, M. A convenient preparation of 1-aroylpiperazines. *Org. Prep. Proced. Int.,* 1976, 8, 85–86. (b) Adamczyk, M.; Fino, J. R. Synthesis of procainamide metabolites. N-acetyl desethylprocainamide and desethylprocainamide. *Org. Prep. Proced. Int.* 1996, 28, 470–474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419–6422. (d) Wang, T.; Zhang, Z.; Meanwell, N. A. Benzoylation of Dianions: Preparation of mono-Benzoylated Symmetric Secondary Diamines. *J. Org. Chem.,* 1999, 64, 7661–7662.
28. Li, H.; Jiang, X.; Ye, Y. -H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.,* 1999, 1, 91–93.
29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.,* 1997, 45, 134–137.
30. Schneller, S. W.; Luo, J. -K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.,* 1980, 45, 4045–4048.
31. Shiotani, S.; Tanigochi, K. Furopyridines. XXII [1]. Elaboration of the C-substitutents alpha to the heteronitrogen atom of furo[2,3-b]-, -[3.2-b]-, -[2.3-c]-and -[3,2-c]pyridine. *J. Het. Chem.,* 1997, 34, 901–907.

32. Minakata, S.; Komatsu, M.; Ohshiro, Y. Regioselective functionalization of 1H-pyrrolo[2,3-b]pyridine via its N-oxide. *Synthesis*, 1992, 661–663.
33. Klemm, L. H.; Hartling, R. Chemistry of thienopyridines. XXIV. Two transformations of thieno[2,3-b]pyridine 7-oxide (1). *J. Het. Chem.*, 1976, 13, 1197–1200.
34. Antonini, I.; Claudi, F.; Cristalli, G.; Franchetti, P.; Crifantini, M.; Martelli, S. Synthesis of 4-amino-1-□-D-ribofuranosyl-1H-pyrrolo[2,3-b]pyridine (1-Deazatubercidin) as a potential antitumor agent. *J. Med. Chem.*, 1982, 25, 1258–1261.
35. (a) Regnouf De Vains, J. B.; Papet, A. L.; Marsura, A. New symmetric and unsymmetric polyfunctionalized 2,2'-bipyridines. *J. Het. Chem.*, 1994, 31, 1069–1077. (b) Miura, Y.; Yoshida, M.; Hamana, M. Synthesis of 2,3-fused quinolines from 3-substituted quinoline 1-oxides. Part II, *Heterocycles*, 1993, 36, 1005–1016. (c) Profft, V. E.; Rolle, W. Uber 4-merkaptoverbindungendes 2-methylpyridins. *J. Prakt. Chem.*, 1960, 283 (11), 22–34.
36. Nesi, R.; Giomi, D.; Turchi, S.; Tedeschi, P., Ponticelli, F. A new one step synthetic approach to the isoxazolo[4,5-b]pyridine system. *Synth. Comm.*, 1992, 22, 2349–2355.
37. (a) Walser, A.; Zenchoff, G.; Fryer, R. I. Quinazolines and 1,4-benzodiazepines. 75. 7-Hydroxyaminobenzodiazepines and derivatives. *J. Med. Chem.*, 1976, 19, 1378–1381. (b) Barker, G.; Ellis, G. P. Benzopyrone. Part I. 6-Amino- and 6-hydroxy-2-subtituted chromones. *J. Chem. Soc.*, 1970, 2230–2233.
38. Ayyangar, N. R.; Lahoti, R J.; Daniel, T. An alternate synthesis of 3,4-diaminobenzophenone and mebendazole. *Org. Prep. Proced. Int.*, 1991, 23, 627–631.
39. Mahadevan, I.; Rasmussen, M. Ambident heterocyclic reactivity: The alkylation of pyrrolopyridines (azaindoles, diazaindenes). *Tetrahedron*, 1993, 49, 7337–7352.
40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.*, 1994, 68, 654–660.
41. Bodanszky, M.; Bodanszky, A. *"The Practice of Peptide Synthesis"* 2$^{nd}$ Ed., Springer-Verlag: Berlin Heidelberg, Germany, 1994.
42. Albericio, F. et al. *J. Org. Chem.* 1998, 63, 9678.
43. Knorr, R. et al. *Tetrahedron Lett.* 1989, 30, 1927.
44. (a) Jaszay Z. M. et al. *Synth. Commun.*, 1998 28, 2761 and references cited therein; (b) Bernasconi, S. et al. *Synthesis*, 1980, 385.
45. (a) Jaszay Z. M. et al. *Synthesis*, 1989, 745 and references cited therein; (b) Nicolaou, K. C. et al. *Angew. Chem. Int. Ed.* 1999, 38, 1669.
46. Ooi, T. et al. *Synlett.* 1999, 729.
47. Ford, R. E. et al. *J. Med. Chem.* 1986, 29, 538.
48. (a) Yeung, K. -S. et al. Bristol-Myers Squibb Unpublished Results. (b) Wang, W. et al. *Tetrahedron Lett.* 1999, 40, 2501.
49. Brook, M. A. et al. *Synthesis*, 1983, 201.
50. Yamazaki, N. et al. *Tetrahedron Lett.* 1972, 5047.
51. Barry A. Bunin "The Combinatorial Index" 1998 Academic Press, San Diego/London pages 78–82.
52. Richard C. Larock Comprehensive Organic Transformations 2nd Ed. 1999, John Wiley and Sons New York.
53. M. D. Mullican et.al. *J.Med. Chem.* 1991, 34, 2186–2194.
54. Protective groups in organic synthesis 3rd ed./Theodora W. Greene and Peter G. M. Wuts. New York: Wiley, 1999.
55. Katritzky, Alan R. Lagowski, Jeanne M. The principles of heterocyclic Chemistry New York: Academic Press, 1968
56. Paquette, Leo A. Principles of modern heterocyclic chemistry New York: Benjamin.
57. Katritzky, Alan R.; Rees, Charles W.; Comprehensive heterocyclic chemistry: the structure, reactions, synthesis, and uses of heterocyclic compounds 1st ed.Oxford (Oxfordshire) ; New York: Pergamon Press, 1984. 8 v.
58. Katritzky, Alan RHandbook of heterocyclic 1st edOxford (Oxfordshire); New York: Pergamon Press, 1985.
59. Davies, David I Aromatic Heterocyclic Oxford; New York: Oxford University Press, 1991.
60. Ellis, G. P. Synthesis of fused Chichester [Sussex]; New York: Wiley, c1987–c1992. Chemistry of heterocyclic compounds ; v. 47.
61. Joule, J. A Mills, K., Smith, G. F. Heterocyclic Chemistry, 3rd ed London ;New York Chapman & Hall, 1995.
62. Katritzky, Alan R., Rees, Charles W., Scriven, Eric F. V. Comprehensive heterocyclic chemistry II: a review of the literature 1982–1995.
63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles: structure, reactions, syntheses, and applications Stuttgart; New York: G. Thieme, 1995.
65. Grimmett, M. R. Imidazole and benzimidazole Synthesis London; San Diego: Academic Press, 1997.
66. Advances in heterocyclic chemistry. Published in New York by Academic Press, starting in 1963–present.
67. Gilchrist, T. L. (Thomas Lonsdale) Heterocyclic chemistry 3rd ed. Harlow, Essex: Longman, 1997.414 p.: ill.; 24 cm.
68. Farina, Vittorio; Roth, Gregory P. Recent advances in the Stille reaction; *Adv. Met. -Org. Chem.* 1996, 5, 1–53.
69. Farina, Vittorio; Krishnamurthy, Venkat; Scott, William J. The Stille reaction; Org. React. (N.Y.) (1997), 50, 1–652.
70. Stille, J. K. *Angew. Chem. Int. Ed. Engl.* 1986, 25, 508–524.
71. Norio Miyaura and Akiro Suzuki *Chem Rev.* 1995, 95, 2457.
72. Home, D. A. *Heterocycles* 1994, 39, 139.
73. Kamitori, Y. et. al. *Heterocycles*, 1994, 37(1), 153.
74. Shawali, J. *Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et.al. *Indian J Chem.* 1978, 16, 1030.
78. *Chemische Berichte* 1902, 35, 1545.
79. *Chemische Berichte Ibid* 1911, 44, 493.
80. Moubarak, I., Vessiere, R. *Synthesis* 1980, Vol. 1, 52–53.
81. *Ind J. Chem.* 1973, 11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828–5832.
85. Bowden, K. et. al. *J. Chem. Soc.* 1946, 953.
86. Nitz, T. J. et. al. *J. Org. Chem.* 1994, 59, 5828–5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir.

Tetrahedron Lett., 1995, 36, 6419–6422. (c) Jenneskens, L. W.; Mahy, J.; den Berg, E. M. M. de B. -v.; Van der Hoef, I.; Lugtenburg, J. Recl. Trav. Chim. Pays-Bas 1995, 114, 97.

89. Wang, T.; Zhang, Z.; Meanwell, N. A. Benzoylation of Dianions: Preparation of mono-Benzoylated Symmetric Secondary Diamines. J. Org. Chem., 1999, 64, 7661–7662.

90. (a) Adamczyk, M.; Fino, J. R. Synthesis of procainamide metabolites. N-acetyl desethylprocainamide and desethylprocainamide. Org. Prep. Proced. Int. 1996, 28, 470–474. (b) Wang, T.; Zhang, Z.; Meanwell, N. A. Regioselective mono-Benzoylation of Unsymmetrical Piperazines. J. Org. Chem., in press.

91. Masuzawa, K.; Kitagawa, M.; Uchida, H. Bull Chem. Soc. Jpn. 1967, 40, 244–245.

92. Furber, M.; Cooper, M. E.; Donald, D. K. Tetrahedron Lett. 1993, 34, 1351–1354.

SUMMARY OF THE INVENTION

The present invention comprises compounds of Formula I, their pharmaceutical formulations, and their use in patients suffering from or susceptible to a virus such as HIV. The compounds of Formula I, which include nontoxic pharmaceutically acceptable salts and/or hydrates thereof, have the formula and meaning as described below. Each embodiment of a particular aspect of the invention depends from the preceding embodiment unless otherwise stated.

A first embodiment of a first aspect of the present invention are compounds of Formula I, including pharmaceutically acceptable salts thereof,

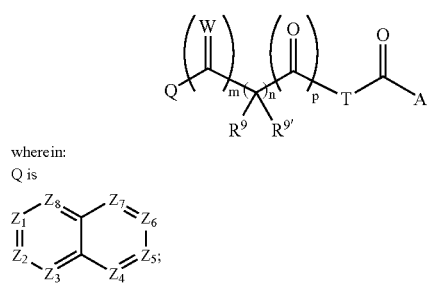

wherein:
Q is

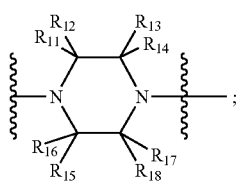

A is selected from the group consisting of $C_{1-6}$alkoxy, $C_{1-6}$alkyl, $C_{3-7}$cycloalkyl, phenyl, and heteroaryl; wherein said heteroaryl may be monocyclic or bicyclic and may be comprised of three to eleven atoms selected from the group consisting of C, N, $NR^9$, O, and S, and wherein each ring of said phenyl and heteroaryl is optionally substituted with one to five same or different substituents selected from the group consisting of $R^{19}$–$R^{23}$;
W is O or —NH;
T is $Z^1$ is $CR^1$ or N;
$Z^2$ is $CR^2$ or N;
$Z^3$ is $CR^3$ or N;
$Z^4$ is $CR^4$ or N;
$Z^5$ is $CR^5$ or N;
$Z^6$ is $CR^6$ or N;
$Z^7$ is $CR^7$ or N;
$Z^8$ is $CR^8$ or N;
$R^1$, $R^2$, $R^3$, $R^4$, $R^5$, $R^6$ $R^7$, and $R^8$ are each independently selected from the group consisting of a bond, hydrogen, halogen, cyano, nitro, $X'R^{24}$, $C_{1-6}$alkyl, $C_{3-7}$cycloalkyl, $C_{2-6}$alkenyl, $C_{4-7}$cycloalkenyl, $C_{2-6}$alkynyl, aryl, heteroaryl, heteroalicyclic, $C(O)NR^{28}R^{29}$, $COR^{25}$ and $CO_2R^{25}$; wherein said $C_{1-6}$alkyl, $C_{3-7}$cycloalkyl, $C_{2-6}$alkenyl, $C_{4-7}$cycloalkenyl, $C_{2-6}$alkynyl, aryl, heteroaryl, and heteroalicyclic are optionally substituted with one to nine same or different halogens or from one to five same or different substituents selected from the substituents comprising group F;

m, n, and p are each independently 0, 1, or 2 provided that the sum of m, n, and p must equal 1 or 2;

F is selected from the group consisting of $C_{1-6}$alkyl, hydroxy, $C_{1-6}$alkoxy, cyano, halogen, benzyl, N-amido, $NR^{30}R^{31}$, $C_{1-6}$alkylC(O)NR$^{30}$R$^{31}$, C(O)NR$^{30}$R$^{31}$, $COOR^{32}$, and $C_{1-6}$alkylCOOR$^{32}$;

$R^9$ and $R^{9'}$ are each independently selected from the group consisting of hydrogen, hydroxy, $C_{1-6}$alkyl, $C_{1-6}$alkoxy, cyano, and fluoro; or $R^9$ and $R^{9'}$ taken together with the carbon atom to which they are attached form —C=O, C=S, C=NOR$^{10}$, —C=NH, or a 3 or 4 membered ring which may contain up to 1 heteroatom chosen from O, N, S;

$R^{10}$ is hydrogen or $C_{1-6}$alkyl;

$R^{11}$, $R^{12}$, $R^{13}$, $R^{14}$, $R^{15}$, $R^{16}$, $R^{17}$, and $R^{18}$ are each independently selected from the group consisting of hydrogen, $CH_2F$ and $C_{1-3}$alkyl; or one of $R^{11}$ and $R^{12}$, $R^{13}$ and $R^{14}$, $R^{15}$ and $R^{16}$ or $R^{17}$ and $R^{18}$ taken together with the carbon atom to which they are attached may form —C=O;

X' is selected from the group consisting of $NR^{10}$, O, and S;

$R^{19}$, $R^{20}$, $R^{21}$, $R^{22}$, and $R^{23}$ are each independently selected from the group consisting of hydrogen, $C_{1-6}$alkyl, $C_{2-6}$alkenyl, $C_{2-6}$alkynyl, halogen, cyano, $X'R^{26}$, trifluoromethyl, and trifluoromethoxy, wherein each of said $C_{1-6}$alkyl, $C_{2-6}$alkenyl, and $C_{2-6}$alkynyl are optionally substituted with one to three same or different substituents selected from halogen and $C_{1-6}$alkyl;

$R^{24}$ is hydrogen or $C_{1-6}$alkyl;

$R^{25}$ is selected from the group consisting of hydrogen, $C_{1-6}$alkyl, $C_{3-7}$cycloalkyl, aryl and heteroaryl;

$R^{26}$ is selected from the group consisting of hydrogen, $C_{1-6}$alkyl, $C_{3-7}$cycloalkyl, trifluoromethyl and $C(O)R^{27}$;

$R^{27}$ is selected from the group consisting of $C_{1-6}$alkyl, $NH_2$ and —$NHC_{1-3}$alkyl;

$R^{28}$ and $R^{29}$ are each independently selected from the group consisting of hydrogen, $SO_2C_{1-6}$alkyl, $C_{1-6}$alkyl, $C_{3-7}$cycloalkyl, aryl, heteroaryl, and heteroalicyclic wherein said $C_{1-6}$alkyl, $C_{3-7}$cycloalkyl, aryl, heteroaryl, and heteroalicyclic are optionally substituted with one to nine same or different halogens or $C_{1-6}$alkyl groups;

$R^{30}$ and $R^{31}$ are each independently selected from the group consisting of hydrogen, $C_{1-6}$alkyl, $C_{3-7}$cycloalkyl, aryl, wherein said $C_{1-6}$alkyl, $C_{3-7}$cycloalkyl, and aryl are optionally substituted with one to nine same or different halogens;

$R^{32}$ is selected from the group consisting of hydrogen, $C_{1-6}$alkyl, and $C_{3-7}$cycloalkyl;

provided that at any given time only one of the members selected from the group consisting of $R^1$, $R^2$, $R^3$, $R^4$, $R^5$, $R^6$, $R^7$ and $R^8$ is a bond, and further provided that said bond is the point of attachment to the adjacent carbon atom in the compound of Formula I.

A second embodiment of the first aspect of the present invention are compounds of Formula I, including pharmaceutically acceptable salts thereof, wherein:
T is

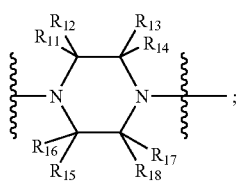

$R^{11}$, $R^{12}$, $R^{13}$, $R^{14}$, $R^{15}$, $R^{16}$, $R^{17}$, and $R^{18}$ are each independently hydrogen or methyl;
W is O; and
A is phenyl or heteroaryl.

A third embodiment of the first aspect of the present invention are compounds of Formula I, including pharmaceutically acceptable salts thereof, wherein:
$R^9$ and $R^{9'}$ are each independently hydrogen or cyano.

A fourth embodiment of the first aspect of the present invention which depends from the second embodiment, are compounds of Formula I, including pharmaceutically acceptable salts thereof, wherein:
m is 1; n is 0; and p is 1.

A fifth embodiment of the first aspect of the present invention, which depends from the second embodiment of the first aspect, are compounds of Formula I, including pharmaceutically acceptable salts thereof, wherein:
m is 1; n is 0; p is 1;
Q is

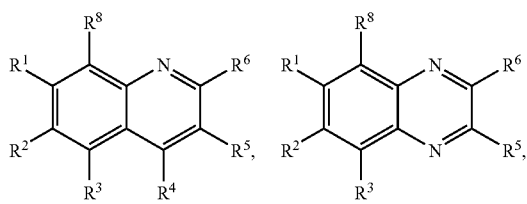

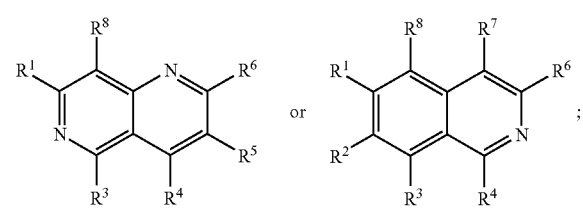

and $R^6$ is a bond for point of attachment.

A sixth embodiment of the first aspect of the present invention, which depends from the fifth embodiment of the first aspect, are compounds of Formula I, including pharmaceutically acceptable salts thereof, wherein:

Q is

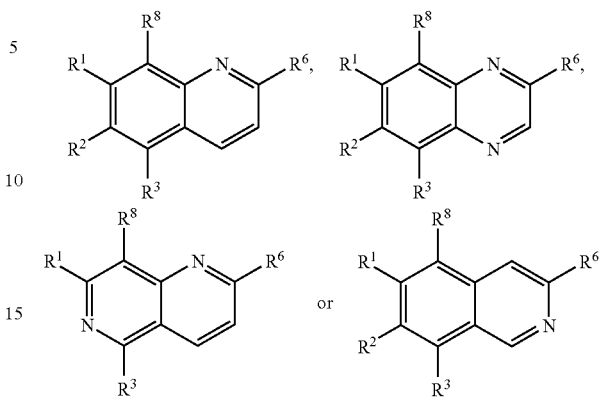

A seventh embodiment of the first aspect of the present invention, which depends from the fifth embodiment of the first aspect, are compounds of Formula I, including pharmaceutically acceptable salts thereof, wherein:
Q is

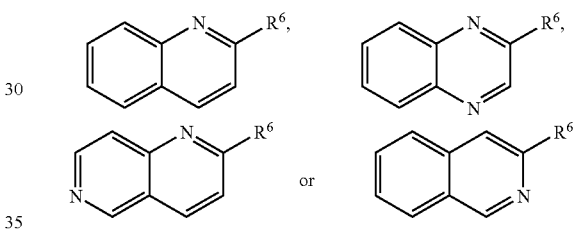

Another embodiment are compounds I wherein
Q is:

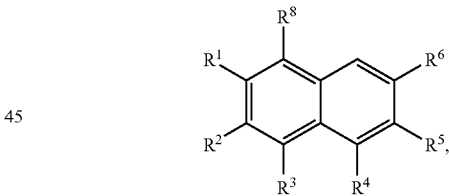

and $R^6$ is a bond for point of attachment.

Another embodiment are compounds I wherein one of $Z_1$ through $Z_8$ is N.

Another embodiment are compounds I wherein two of $Z_1$ through $Z_8$ is N.

A first embodiment of the second aspect of the present invention is a pharmaceutical composition which comprises an antiviral effective amount of a compound of Formula I, including pharmaceutically acceptable salts thereof, as defined in any of the first through sixth embodiments of the first aspect of the present invention, and one or more pharmaceutically acceptable carriers, excipients or diluents.

A second embodiment of the second aspect of the present invention is the pharmaceutical composition of the first embodiment of the second aspect, useful for treating infection by HIV, which additionally comprises an antiviral effective amount of an AIDS treatment agent selected from the group consisting of an AIDS antiviral agent; an anti-infective agent; an immunomodulator; and HIV entry inhibitors.

A first embodiment of a third aspect of the present invention is a method for treating a mammal infected with a virus, comprising administering to said mammal an antiviral effective amount of a compound of Formula I, including pharmaceutically acceptable salts thereof, as defined in any of the first through sixth embodiments of the first aspect of the present invention, and one or more pharmaceutically acceptable carriers, excipients or diluents.

A second embodiment of a third aspect of the present invention is the method of the first embodiment of the third aspect, comprising administering to said mammal an antiviral effective amount of a compound of Formula I, in combination with an antiviral effective amount of an AIDS treatment agent selected from the group consisting of: an AIDS antiviral agent; an anti-infective agent; an immunomodulator; and an HIV entry inhibitor.

The third embodiment of a third aspect of the present invention is the method of either the first or second embodiment of the third aspect, wherein said virus is HIV.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

Definitions

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are furyl, thienyl, benzothienyl, thiazolyl, imidazolyl, oxazolyl, oxadiazolyl, thiadiazolyl, benzthiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, and pyrazinyl.

As used herein, a "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl.

An "alkyl" group refers to a saturated aliphatic hydrocarbon including straight chain and branched chain groups. Preferably, the alkyl group has 1 to 20 carbon atoms (whenever a numerical range; e.g., "1–20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. For example, the term "$C_{1-6}$alkyl" as used herein and in the claims (unless specified otherwise) mean straight or branched chain alkyl groups such as methyl, ethyl, propyl, isopropyl, butyl, isobutyl, t-butyl, amyl, hexyl and the like.

A "cycloalkyl" group refers to a saturated all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclohexane, cycloheptane, and adamantane.

A "cycloalkenyl" group refers to an all-carbon monocyclic or fused ring (i.e., rings which share and adjacent pair of carbon atoms) group wherein one or more rings contains one or more carbon-carbon double bonds but does not have a completely conjugated pi-electron system. Examples, without limitation, of cycloalkenyl groups are cyclopentene, cyclohexadiene, and cycloheptatriene.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "O-carboxy" group refers to a R"C(O)O-group, with R" as defined herein.

An "amino" group refers to an —$NH_2$ group.

A "N-amido" group refers to a $R^xC(=O)NR^y$-group, with $R^x$ selected from the group consisting of alkyl, cycloalkyl, aryl, heteroaryl, and heteroalicyclic and $R^y$ selected from hydrogen or alkyl.

A "cyano" group refers to a —CN group.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |

-continued

ANTIVIRALS

| Drug Name | Manufacturer | Indication |
|---|---|---|
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |
| Tenofouir disoproxil | Gilead | HIV infection, AIDS, (reverse transcriptase inhibitor) |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |

-continued

IMMUNOMODULATORS

| Drug Name | Manufacturer | Indication |
|---|---|---|
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |

| ANTI-INFECTIVES | | |
|---|---|---|
| Drug Name | Manufacturer | Indication |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in Drugs Of The Future 1999, 24(12), pp. 1355–1362; Cell, Vol. 9, pp. 243–246, Oct. 29, 1999; and Drug Discovery Today, Vol. 5, No. 5, May 2000, pp. 183–194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The preparative procedures and anti-HIV-1 activity of the novel heterocyclic amidopiperazine derivatives of Formula I are summarized below.

Abbreviations

The following abbreviations, most of which are conventional abbreviations well known to those skilled in the art, are used throughout the description of the invention and the examples. Some of the abbreviations used are as follows:

| | |
|---|---|
| h = | hour(s) |
| rt = | room temperature |
| mol = | mole(s) |
| mmol = | millimole(s) |
| g = | gram(s) |
| mg = | milligram(s) |
| mL = | milliliter(s) |
| TFA = | Trifluoroacetic Acid |
| DCE = | 1,2-Dichloroethane |
| $CH_2Cl_2$ = | Dichloromethane |
| TPAP = | tetrapropylammonium perruthenate |
| THF = | Tetrahydofuran |
| DEPBT = | 3-(Diethoxyphosphoryloxy)-1,2,3-benzotriazin-4(3H)-one |
| DMAP = | 4-dimethylaminopyridine |
| P-EDC = | Polymer supported 1-(3-dimethylaminopropyl)-3-ethylcarbodiimide |
| EDC = | 1-(3-dimethylaminopropyl)-3-ethylcarbodiimide |
| DMF = | N,N-dimethylformamide |
| Hunig's Base = | N,N-Diisopropylethylamine |
| mCPBA = | meta-Chloroperbenzoic Acid |
| azaindole = | 1H-Pyrrolo-pyridine |
| PMB = | 4-Methoxybenzyl |
| DDQ = | 2,3-Dichloro-5,6-dicyano-1,4-benzoquinone |
| OTf = | Trifluoromethanesulfonoxy |
| NMM = | 4-Methylmorpholine |
| PIP-COPh = | 1-Benzoylpiperazine |
| NaHMDS = | Sodium hexamethyldisilazide |
| EDAC = | 1-(3-Dimethylaminopropyl)-3-ethylcarbodiimide |
| TMS = | Trimethylsilyl |
| DCM = | Dichloromethane |

Chemistry

The present invention comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes.

Preparation of Compounds of Formula I

It should be noted that in many cases reactions are depicted for only one position of an intermediate, such as the $R_5$ position, for example. It is to be understood that such reactions could be used at other positions, such as $R_1$–$R_8$, of the various intermediates. Reaction conditions and methods given in the specific examples are broadly applicable to compounds with other substitution and other tranformations in this application.

Scheme 1
A General method for the Synthesis of Some Compounds of Formula I

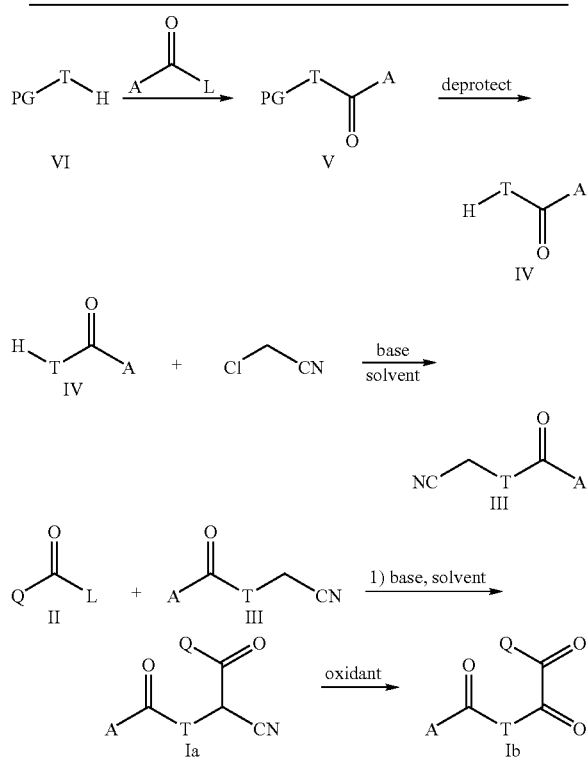

Two general literature references for some of the chemistry depicted in Scheme 1 is Takahashi, K.; Shibasaki, K.; Ogura, K.; Iida, H.; *Chem Lett.* 1983, 859 or Yang; Z.; Zhang, Z.; Meanwell, N. A.; Kadow, J. F.; Wang, T.; *Org. Lett.* 2002, published in the web edition, hard copy in press.

Schemes 1 through 4c describe general reaction schemes for preparing various compounds of Formula I. While these schemes are very general, other permutations such as carrying a precursor or precursors to substituents $R^1$ through $R^7$ through the reaction scheme and then converting it to a compound of Formula I in the last step are also contemplated methods of this invention. Nonlimiting examples of such strategies follow in subsequent schemes.

Scheme 1, and 2 depict a general method suitable for the synthesis of many of the compounds of formula I. As shown in these schemes, a suitable protected piperazine derivative, PG-TH, of Formula VI, (wherein PG is an appropriate amine protecting group) is acylated with an appropriate acylating agent, AC(O)L, (wherein L is a suitable leaving group) to provide the protected acylated piperazine derivative of Formula V. Compound V is then deprotected using standard methods to provide the acylated piperazine derivative of Formula IV. For example, when PG represents tertiary-butoxycarbonyl the compound of Formula V can be deprotected to provide a compound of Formula IV by treatment with a strong acid, such as trifluoroacetic acid or hydrochloric acid, in an appropriate solvent such as dichloromethane. Alternatively, when PG represents benzyl the deprotection may be effected by hydrogenation. The acylpiperazine derivative of Formula IV is then alkylated with 2-chloroacetonitrile in the presence of an appropriate base, such as triethylamine, 4-methylmorpholine or diisopropylethyl amine in an appropriate solvent, such as THF, to provide the cyanomethyl acylpiperazine derivative of Formula III. Reaction of a heterocyclic derivative of formula II (wherein L is an appropriate leaving group, such as $OCH_3$) with an anion of the cyanomethyl acylpiperizine of Formula III, provides cyanomethyl amide derivative of Formula Ia. Oxidation of the cyanomethyl amide derivative of Formula Ia to a ketoamide derivative of Formula Ib is carried out preferentially using a peracid such as meta-chloroperoxybenzoic acid (mCPBA). The cheap and simple oxidant sodium hypochlorite solution (common bleach) is also useful.

Other peracids could also be utilized for the oxidation of a compound of Formula Ia to a compound of Formula Ib, including peroxy acetic acid generated in situ. Other methods for oxidation are shown in the following Table A which describes a one pot condensation/oxidation process which is usually preferred:

TABLE A

Oxidation Conditions

Oxidation Conditions mCPBA (1 eq.)
mCPBA (1.5 eq.)
mCPBA (2 eq.)
Oxone (2 eq., with $H_2O$)
$H_2O_2$ (2 eq., 30% in $H_2O$)
$H_2O_2$-Urea (2 eq.)
AcOOH (2 eq., 32% in AcOH)
Clorox ™
(2 eq., 5.25% NaOCl)

Compounds of Formula II can be esters, preferably methyl esters, however other simple alkyl esters or activated acid derivatives such as acid chlorides, acid anhydrides, or Weinreb amides could also find utility in preparing compounds as shown.

Scheme 2 depicts a general method suitable for the synthesis of many of the compounds of Formula I using the methodology described for Scheme 1. As shown in Scheme 1, a piperazine derivative of formula IV may be alkylated with chloroacetonitrile in the presence of a suitable base, such as triethylamine, in an appropriate aprotic solvent, such as tetrahydrofuran, to provide a cyanomethylpiperazine derivative of formula III. Other tertiary amine bases such as 4-methylmorpholine may also be used in this step. Reaction of a suitable heterocyclic carboxylate ester of formula II with an anion of a cyanomethyl piperazine derivative provides cyanomethyl esters of formula Ia. The anion of the cyanomethyl piperazine derivative can be generated by treating a solution of the cyanomethyl piperazine derivative with an appropriate base, such as sodium hexamethyldisilazide (NaHMDS). The esters of formula II are preferably methyl esters but other simple alkyl esters or activated acid derivatives such as acid chlorides, acid anhydrides, or Weinreb amides could also find utility. Thus, for example, L in Scheme 1 can be OR', where R' is $C_{1-6}$ alkyl, with methyl preferred. Oxidation of the alpha cyano ketone of Formula Ia to a ketoamide of Formula Ib is carried out using a peracid oxidant such as meta-chloroperoxybenzoic acid. Other peracids may be useful for the oxidation of Ia to Ib, including peroxy acetic acid generated in situ. In addition other preferred methods such as bleach were described above.

Scheme 2
A General method for the Synthesis of Compounds of Formula I

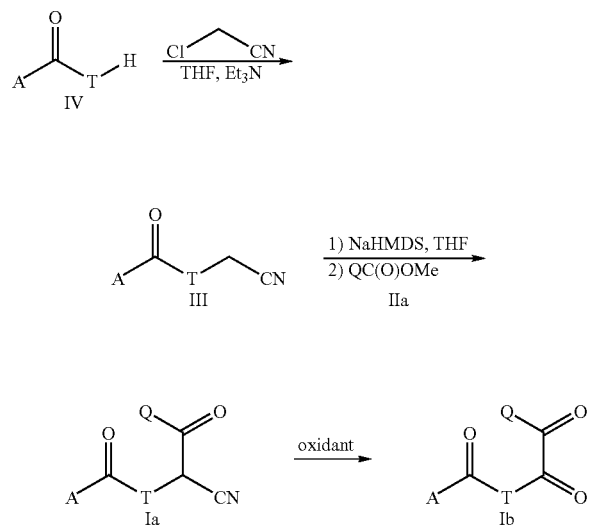

Alternatively, as shown in Scheme 3 below, compounds of formula Ib can be prepared by reaction of a heterocyclic glyoxylic acid derivative of Formula VII (QC(O)CO$_2$H), with a piperazine derivative of Formula IV (HTC(O)A), under standard peptide coupling conditions to provide compounds of Formula Ib. Standard peptide coupling refers to coupling an amine with a carboxylic acid in the presence of an amine acid coupling reagent such as DCC, PyBop, EDC, or DEPBT. The preparation of DEPBT is described by Li, H.; Jiang, X.; Ye, Y. -H.; Fan, C.; Romoff, T.; and Goodman, M. in *Organic Lett.*, 1999, 1, 91–93.

One preferred method for carrying out this reaction is to use the reagent 3-(diethoxyphosphoryloxy)-1,2,3-benzotriazin-4(3H)-one (DEPBT) and an amine HTC(O)A in DMF as solvent containing a tertiary amine such as diisopropylethylamine. Another preferred method is to use the reagent 1-(3-Dimethylaminopropyl)-3-ethylcarbodiimide hydrochloride in an appropriate solvent and in the presence of diisopropylethylamine. Typical stoichiometries are given in the specific examples but these ratios may be modified. The amide bond construction reactions depicted in Scheme 3 could be carried out using the specialized conditions described herein or alternatively by applying the conditions or coupling reagents for amide bond construction described in the literature. Some specific non-limiting examples are given in this application.

Scheme 3
Glyoxylic acid method for preparation of compounds of Formula Ib

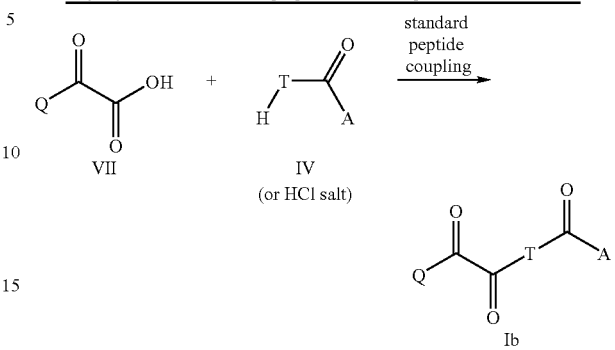

Another method for the synthesis of compounds of Formula Ib is shown in Scheme 4, below. The hydrolysis of the heterocyclic oxoacetic acid ester intermediate of Formula VIII, to form the heterocyclic oxoacetic acid of Formula VII, is shown in Step 1 of Scheme 4. The usual conditions employ methanolic or ethanolic sodium hydroxide followed by acidification with aqueous hydrochloric acid of varying molarity but 1M HCl is preferred. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as CH$_2$Cl$_2$ or THF in the presence of Triton B. Temperatures of –70° C. to the boiling point of the solvent may be employed but –10° C. is preferred. Other conditions for ester hydrolysis are well known to chemists of average skill in the art. It is to be understood that these hydrolysis conditions are applicable to other regioisomeric heterocyclic oxoacetic acid esters. The glyoxylic acid derivative of Formula VII may then be converted to a compound of Formula Ib directly as described in Scheme 3, above. Alternatively, as Step 2 of Scheme 4 depicts, the glyoxylic acid derivative of Formula VII can be converted to the corresponding glyoxylic acid chloride of Formula IX. This transformation can be carried out using thionyl chloride, reaction with oxalyl chloride, or other methods well known in the art. Alternatively, the intermediates of Formula IX can also be obtained as described hereinafter for Scheme I-29. Coupling of the piperazine derivative, H-T-C(O)A to the intermediate glyoxylic acid chloride of Formula IX, may be carried out in a basic solvent such as pyridine or triethylamine, or in an inert solvent in the presence of pyridine as base or other tertiary amine bases to provide compounds of Formula Ib. Schotten-Baumann conditions could also be employed for this coupling (aqueous base).

Scheme 4
Glyoxylic acid chloride method

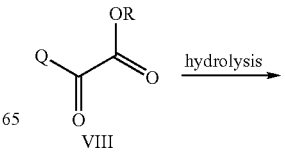

-continued

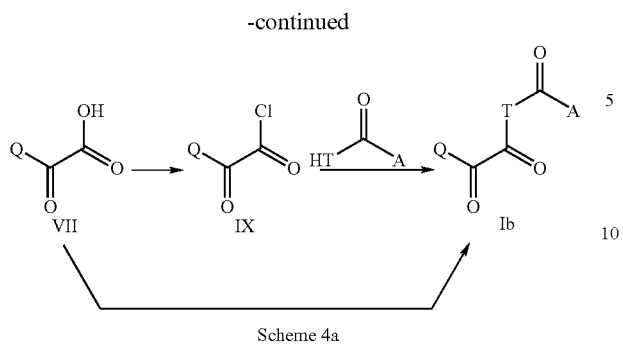

Scheme 4a
Alternate method for the Synthesis of Compounds of Formula I

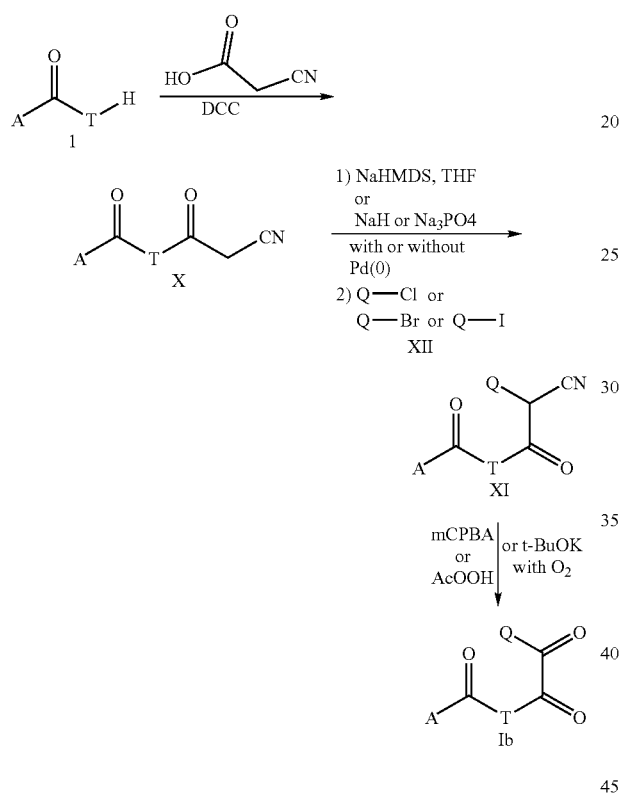

Ref.
For the Pd(0)-mediated cross coupling: Beare, N. A.; Hartwig, J. F.; J. Org. Chem. 2002, 67, 541
For the SnAr-type reactions:
For oxidation:

Scheme 4b
A General method for the Synthesis of Other Compounds of Formula 1

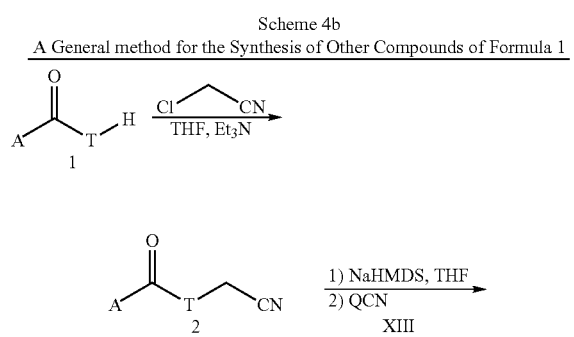

-continued

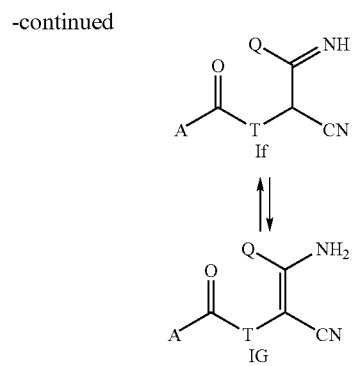

Scheme 4c
A more specific synthesis of compounds of Formula 1

Synthesis of Intermediates

It should be noted that in many cases reactions are depicted for only one position of an intermediate or compound of Formula I, such as the $R^6$ position, for example. It is to be understood that such reactions could be used at other positions, such as $R^1$–$R^4$ or $R^7$ of the various intermediates or compounds of Formula I. Reaction conditions and methods given in the specific examples are broadly applicable to compounds with other substitution and to other tranformations in this application.

Heterocyclic carboxylates of general formula QC(O)OR (such as those of formula IIa in Scheme 1, herein) or suitable surrogates may be purchased from commercial sources or synthesized. Bicyclo 4.4.0 heteroaromatic rings which by definition contain fused aromatic rings are well known in the art. Examples include such compounds as quinolines, isoquinolines, fused pyrimidines etc. Searching scifinder for such compounds produces numerous examples of such substituted and unsubstituted compounds. Some additional examples of pertinent literature are listed below:

Compounds of formula IIa can be prepared by two basic strategies using numerous methods from the literature or the methods within this application. Strategy 1 involves the synthesis of the appropriate compound containing a carboxylate ester while strategy 2 involves the synthesis of the precursor followed by installation of a carboxylate ester moiety. These methods are described in the literature references above or other art.

If desired, the substituents $R^1$ through $R^8$ may be prepared to form either halide, triflate, cyano, carboxaldehyde, carboxylic acid, or carboxylic ester. These groups can be transformed into other compounds of claim 1 using the known methodology for such substituents and some described below.

Katritzky, Alan R.; Rees, Charles W.; Comprehensive heterocyclic chemistry: the structure, reactions, synthesis, and uses of heterocyclic compounds 1$^{st}$ ed.Oxford (Oxfordshire); New York: Pergamon Press, 1984. 8 v.

Katritzky, Alan R., Rees, Charles W. , Scriven, Eric F. V. Comprehensive heterocyclic chemistry II: a review of the literature 1982–1995.

Comprehensive heterocyclic chemistry II: a review of the literature 1982–1995: the structure, reactions, synthesis, and uses of heterocyclic compounds 1st ed Oxford; New York: Pergamon, 1996. 11 v. in 12: ill.;

"Isoquinolines" New York, Wiley, 1981–1995; v. 1–3, Series: Chemistry of heterocyclic compounds; v. 38; Alternate Authors: Grethe, Guenter.

"An Interscience-publication." Pt. 2 edited by F. G. Kathawala, Gary M. Coppola, Herbert F. Schuster. Pt. 3 edited by Gary M. Coppola, Herbert F. Schuster.

The fused bicyclic 4.4.0 aromatic or heteroaromatic carboxylates of formula IIa can be prepared by two basic strategies using numerous methods from the literature or the methods within this application. The first strategy involves the synthesis of an appropriate fused bicyclic aromatic or heteroaromatic ring containing a carboxylate ester group while the second strategy involves the synthesis of the parent heterocycle followed by installation of a carboxylate ester moiety onto the parent ring system. The following Schemes I-1 through I-28 represent various heterocyclic carboxylates which may serve as useful intermediates for the preparation of compounds of Formula I. The methods used to prepare compounds of Formula I from the intermediates are those described for Schemes 1 through 4c.

Schemes I-1 through I-28 depict methods and conditions for the synthesis of intermediate carboxylates according to the first strategy wherein a fused bicyclic containing carboxylate moiety is synthesized. Literature references follow the depicted Schemes.

General Procedures for the Preparation of [6,6] Bicyclic Systems:

The following procedures are examples which can be used to prepare the substituents which form Q or suitable precursors. Note, in Schemes I-1 to I-28, $R_3$–$R_8$ means $R^1$, $R^2$, $R^3$ and $R^8$ corresponding to Compounds I; L of Scheme 1 corresponds to OR'; and $R_7$–$R_6$ corresponds to $R^6$ and $R^7$ in corresponding Compounds I. Also, subscripted R groups (e.g. $R_6$) corresponds to the superscripted R group (e.g. $R^6$) in compounds of Formula I.

A. Procedures to Make Substituted Isoquinilines

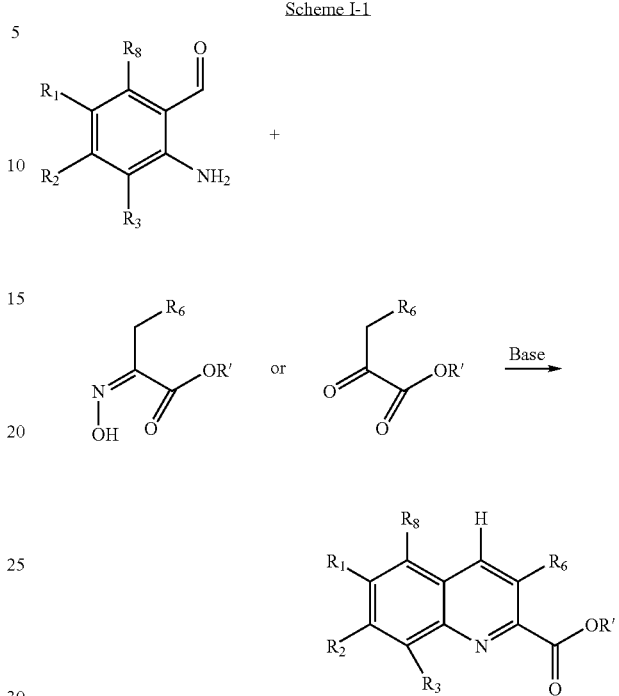

Boger, D. L.; Chen, J. H.; J Org Chem 1995, 60 (22), 7369.

Kende, A. S.; Ebetino, F. H.; Tetrahedron Lett 1984, 25 (9), 923.

Ried, W.; Berg, A.; Schmidt, G.; Chem Ber 1952, 85, 204.

Borsche, W.; Noll, W.; Justus Liebigs Ann Chem 1937, 532, 127.

This could be extended to other series with additional nitrogens in the rings:

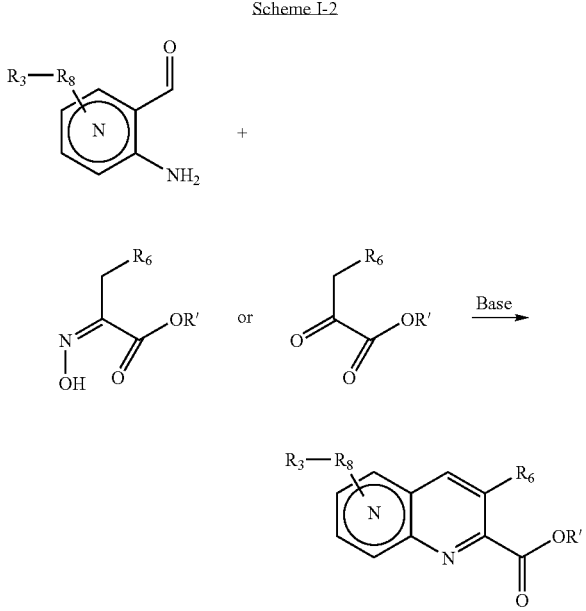

Scheme I-3

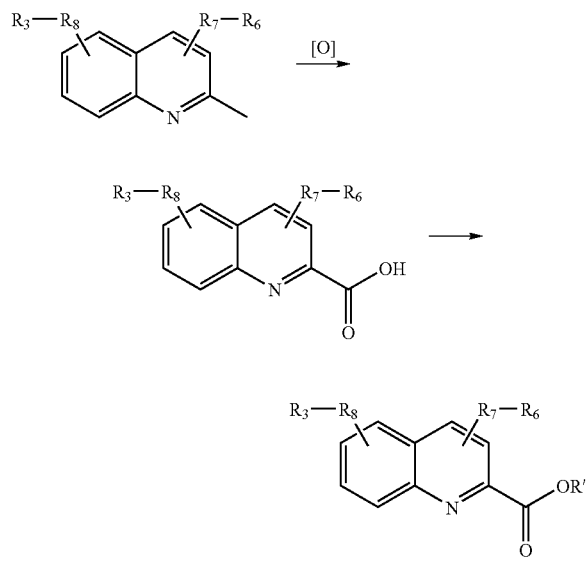

This could be extended to:

Scheme I-4

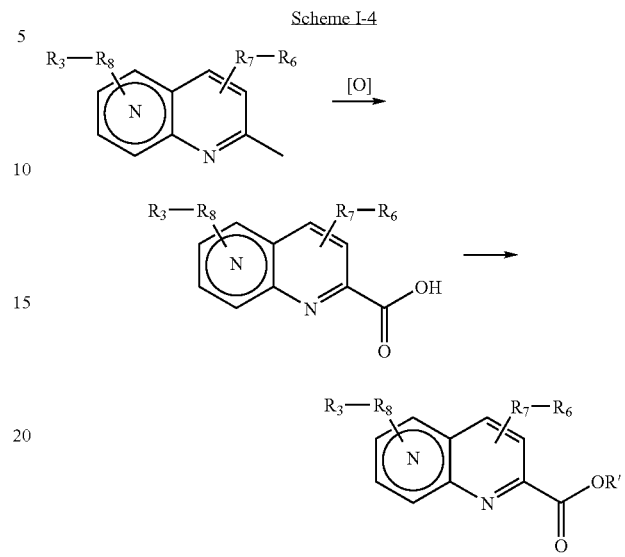

Scheme I-5

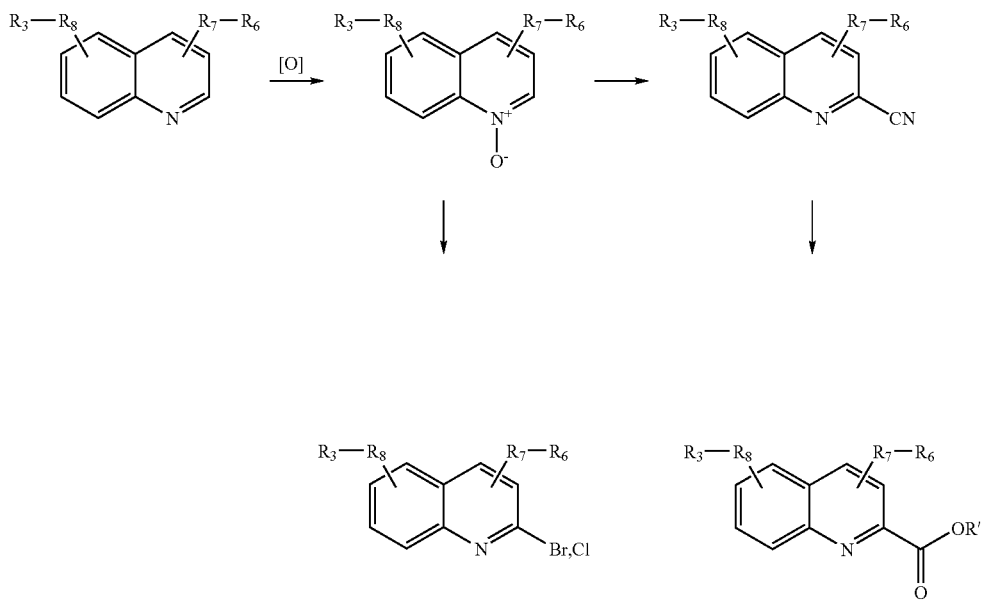

Ferranti, A.; Garuti, L.; Giovanninetti, G.; Roberti, M.; Varoli, L.; Farmaco, Ed Sci 1993, 48 (11), 1547–1553.

Author Not Provided; Synth Commun 1986, 2, 157.

Campbell, K. N.; Helbing, C. H.; Kerwin, J. F.; J Am Chem Soc 1946, 68, 1840.

Spivey, A. M.; Curd, F. H. S.; J Chem Soc 1949, 2656.

Fieser, L. F.; Brown, R. H.; J Am Chem Soc 1949, 71, 3609.

Mattox, V. R.; Kendall, E. C.; J Biol Chem 1951, 188, 287.

Phillips, A. P.; Maggiolo, A.; J Am Chem Soc 1952, 74, 3922.

Roth, R.; Erlenmeyer, H.; Helv Chim Acta 1954, 37, 1064.

Shiba, S. A.; Indian J Chem, Sect B 1995, 34 (10), 895–896.

MIYASHITA, A.; KAWASHIMA, T.; IIJIMA, C.; HIGASHINO, T.;

Heterocycles 1992, 33 (1), 211–218.

Kobayashi, Y.; Kumadaki, I.; Taguchi, S.; Chem Pharm Bull 1969, 17, 2335.

Kaneko, C.; Ochiai, E.; et al.; Chem Pharm Bull 1960, 8, 487.

Feely, W. E.; Beavers, E. M.; J Am Chem Soc 1959, 81, 4004.

Org Synth 1962, 42, 30.

This could be extended to:

Scheme I-6

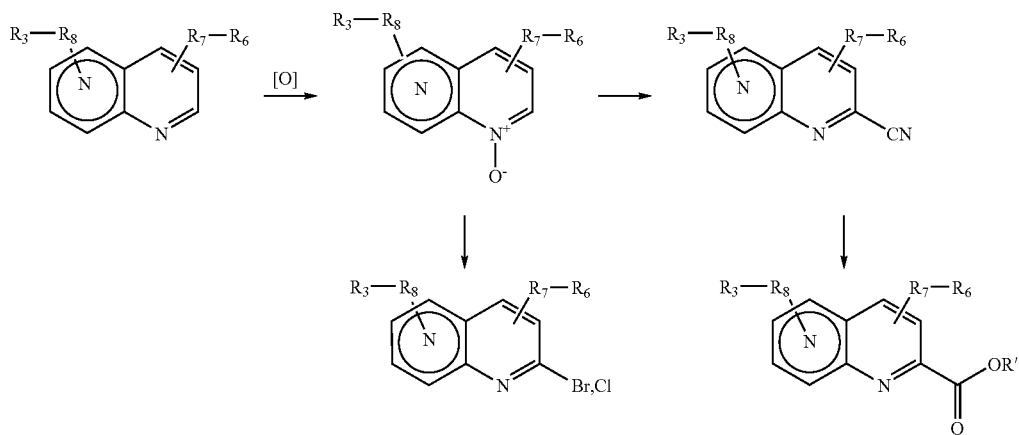

Scheme I-7

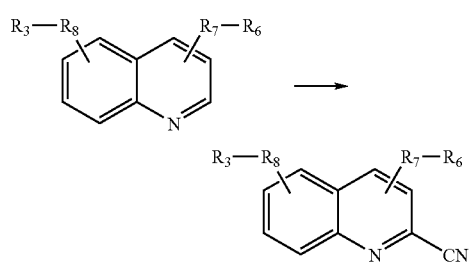

Boger, D. L.; Panek, J. S.; J Am Chem Soc [JACSAT] 1985, 107 (20), 5745.

This could be extended to:

Scheme I-8

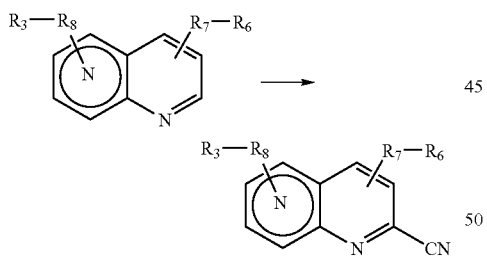

Scheme I-9

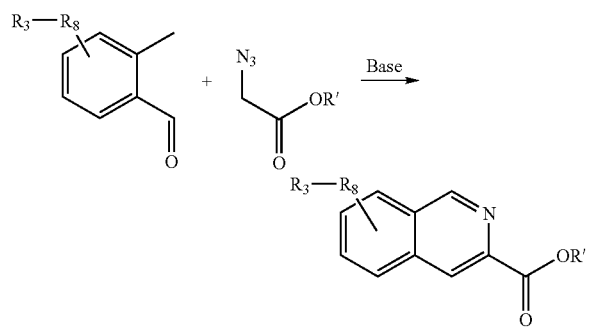

Henn, L.; Hickey, D. M. B.; Moody, C. J.; Rees, C. W.; J Chem Soc, Perkin Trans 1 [JCPRB4] 1984, 2189.

Gilchrist, T. L.; Rees, C. W.; Rodrigues, J. A. R.; J Chem Soc, Chem Commun [JCCCAT] 1979, 627.

Hickey, D. M. B.; Moody, C. J.; Rees, C. W.; J Chem Soc, Chem Commun [JCCCAT] 1982, 1 (14), 3.

This could be extended to:

Scheme I-10

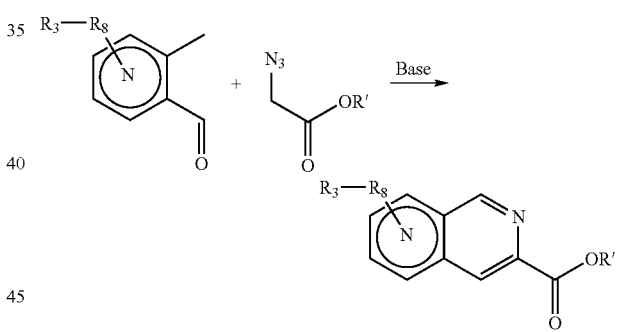

Scheme I-11

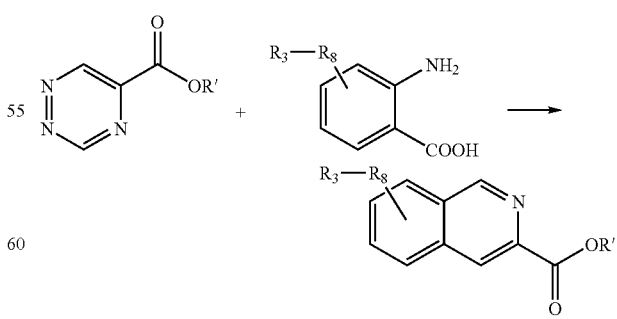

D'A. ROCHA GONSALVES, A. M.; PINHO E MELO, T. M. V. D.; GILCHRIST, T. L.; Tetrahedron 1992, 48 (33), 6821–6826.

This could be extended to:
Scheme I-12
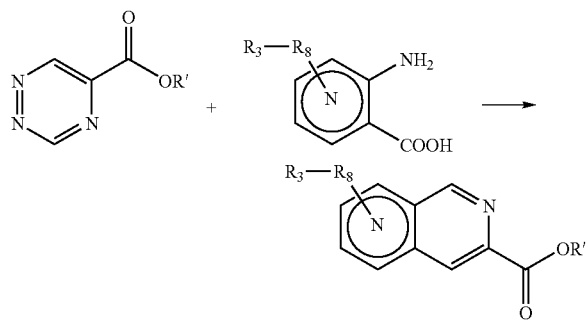
In Schemes I-13 and I-14, R″ is methyl or ethyl.
Scheme I-13
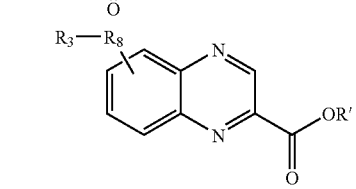
SINGH, S. K.; DEKHANE, M.; LE HYARIC, M.; POTIER, P.; DODD, R. H.; Heterocycles 1997, 44 (1), 379–391.
This could be extended to:
Scheme I-14
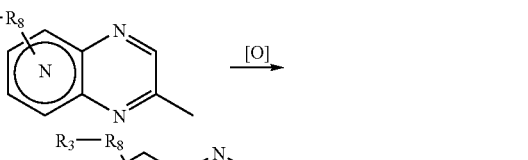
Scheme I-15
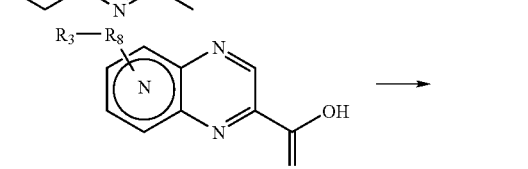
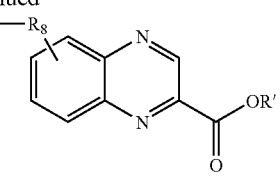
Kepez, M.; Monatsh Chem 1989, 120, 127.
Keller-Schierlein, W.; Prelog, V.; Helv Chim Acta 1957, 40, 205.
This could be extended to:
Scheme I-16
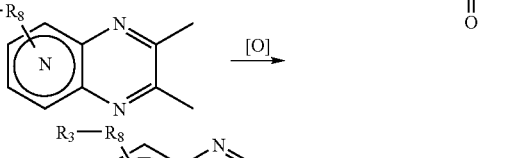

Scheme I-17

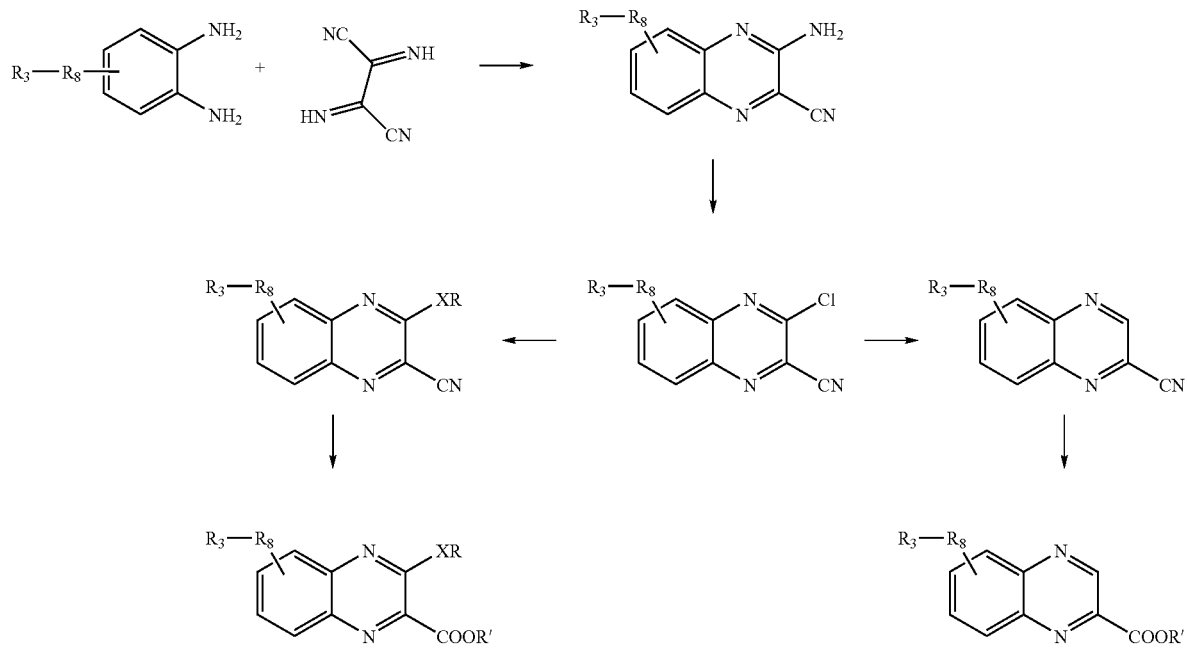

XR=R where $R^6$=$OR^{24}$, $NR^{10}R^{24}$, $SR^{24}$, H.

Begland, R. W.; Hartter, D. R.; J Org Chem [JOCEAH] 1972, 37, 4136.

Monge, A.; Palop, J. A.; Pinol, A.; Martinez-Crespo, F. J.; Narro, S.; Gonzalez, M.; Sainz, Y.; Lopez De Cerain, A.; Hamilton, E.; Barker, A. J.; J Heterocycl Chem [JHTCAD] 1994, 31 (5), 1135–1139.

Monge, A.; Palop, J. A.; Del Castillo, J. C.; Caldero, J. M.; Roca, J.; Romero, G.; Del Rio, J.; Lasheras, B.; J Med Chem [JMCMAR] 1993, 36 (19), 2745–2750.

MAHGOUB, S. A.; Phosphorus, Sulfur Silicon Relat Elem [PSSLEC] 1991, 61, 151–160.

This could be extended to:

Scheme I-18

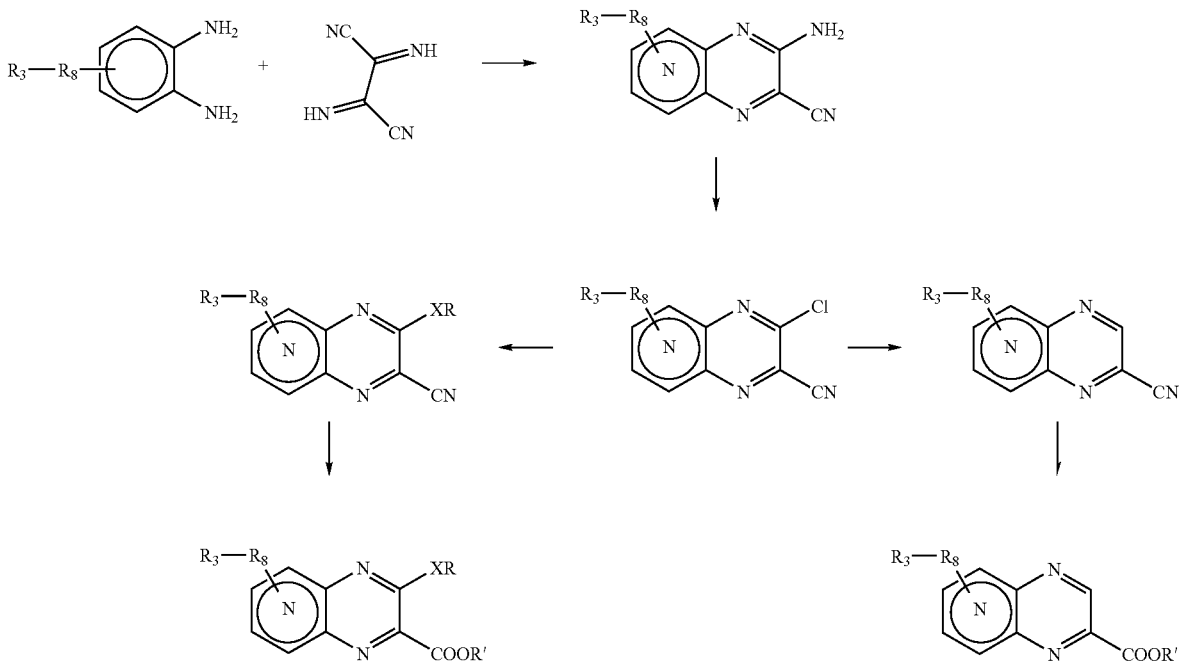

Scheme I-19

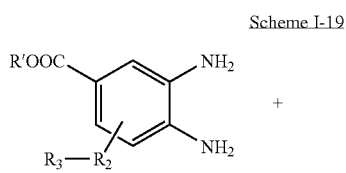

RAO, P. S.; VENKATARATNAM, R. V.; Indian J Chem, Sect B [IJSBDB] 1992, 31 (11), 733–735.

This could be extended to:

Scheme I-20

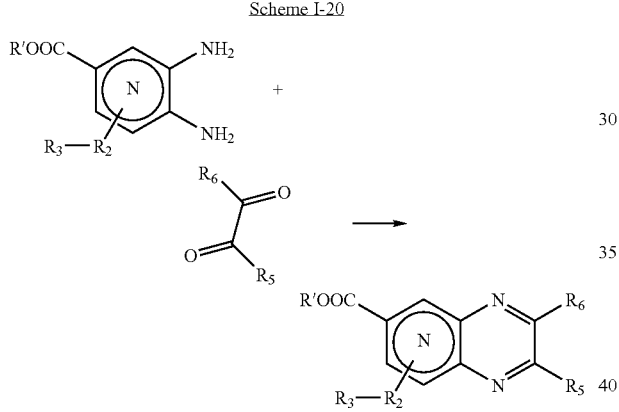

Scheme I-21

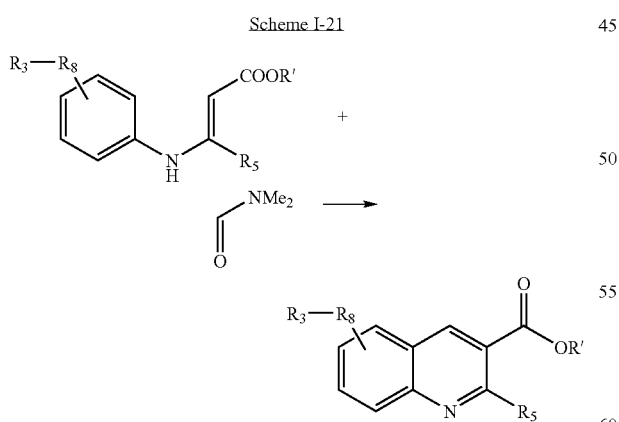

ANZINI, M.; CAPPELLI, A.; VOMERO, S.; GIORGI, G.; LANGER, T.; BRUNI, G.; ROMEO, M. R.; BASILE, A. S.; J Med Chem [JMCMAR] 1996, 39 (21), 4275–4284.

Adams, D.; Dominguez, J.; Lo Russo, V.; De Rekowski, N. M.; Gazz Chim Ital [GCITA9] 1989, 119 (5), 281.

Adams, D. R.; Dominguez, J. N.; Perez, J. A.; Tetrahedron Lett [TELEAY] 1983, 24, 517.

Alonso, M. A.; Del Mar Blanco, M.; Avendano, C.; Menendez, J. C.; Heterocycles [HTCYAM] 1993, 36 (10), 2315–2325.

This could be extended to:

Scheme I-22

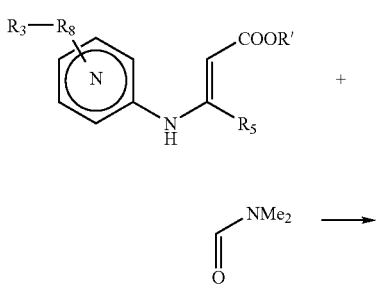

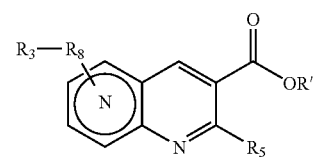

Scheme I-23

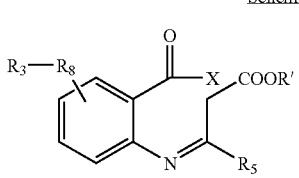

$X = R^7$, where $R^7 = H$, $OR^{24}$, $NR^{10}R^{24}$

Merour, J. Y.; Tatibouet, F.; Synthesis [SYNTBF] 1978, 698.

Lutz, R. E.; et al.; J Am Chem Soc [JACSAT] 1946, 68, 1285.

J Org Chem [JOCEAH] 1950, 15, 317.

J Org Chem [JOCEAH] 1950, 15, 326.

Ind Eng Chem Prod Res Dev [IEPRA6] 1950, 42, 1565.

de Diesbach, H.; Gross, J.; Tschamen, W.; Helv Chim Acta [HCACAV] 1951, 34, 1050.

Borsche, W.; Doeller, W.; Wagner-Roemmich, M.; Ber Dtsch Chem Ges [BDCGAS] 1943, 76, 1099.

Chem Abstr [CHABA8], 1944 (4947)

Baumgarten, H. E.; Saylor, J. L.; J Am Chem Soc [JACSAT] 1957, 79, 1502.

This could be extended to:
Scheme I-24
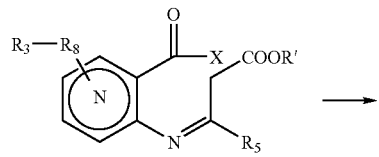
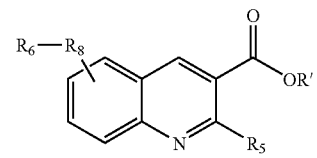
Gazit, A.; Levitzki, A.; et al.; J Med Chem [JMCMAR] 1996, 39 (11), 2170.
This could be extended to:
Scheme I-26
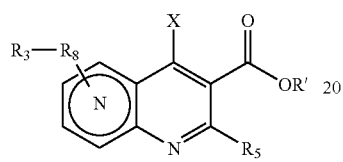
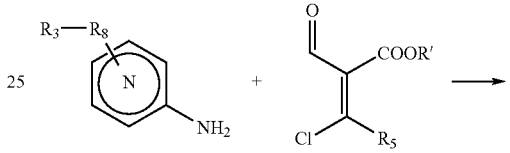
$X = R^7$, where $R^7 = H$, $OR^{24}$, $NR^{10}R^{24}$
Scheme I-25
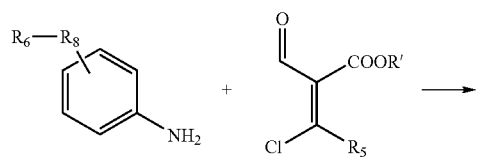
Scheme I-27
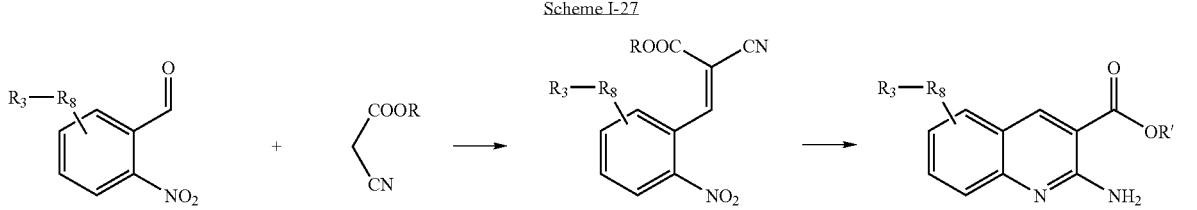
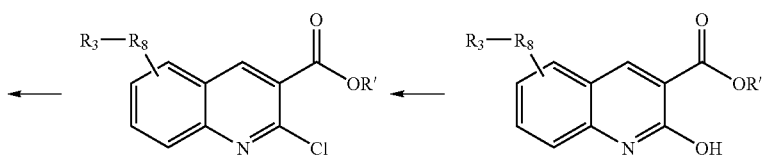

X=$R^5$, where $R^5$=$OR^{24}$, $NR^{10}R^{24}$, $SR^{24}$, H

Rupe, H.; Heckendorn, A.; Helv Chim Acta [HCACAV] 1926, 9, 980.

Ukraintsev, I. V.; Taran, S. G.; Gorokhova, O. V.; Marusenko, N. A.; Kovalenko, S. N.; Turov, A. V.; Filimonova, N. I.; Ivkov, S. M.; Khim Geterotsikl Soedin [KGSSAQ] 1995 (2), 195–203.

Lab Bellon SA Roger; France Patent 1994, 2703681 (FR-2703681), 94-326370.

Alonso, M. A.; Del Mar Blanco, M.; Avendano, C.; Menendez, J. C.; Heterocycles [HTCYAM] 1993, 36 (10), 2315–2325.

RAO, K. R.; BHANUMATHI, N.; SATTUR, P. B.; J Heterocycl Chem [JHTCAD] 1991, 28 (5), 1339–1340.

This could be extended to:

acid chloride derivative of formula QC(O)C(O)Cl can be prepared by treating an appropriate heterocycle of formula Q-H with oxalyl chloride in an appropriate solvent such as diethyl ether in the presence of an appropriate Lewis acid catalyst such as aluminum trichloride The glyoxylic acid chloride derivatives can then be reacted with an appropriately substituted piperazine derivative of formula H-TC(O)A in an appropriate solvent such as tetrahydrofuran or acetonitrile in the presence of a suitable base such as diisopropylethylamine or pyridine to provide compounds of formula I. Additional methodology for attaching the —C(O)C(O)TC(O)A moiety to an appropriate heterocycle is described in WO-0076521 published by the World Patent Office on Dec. 12, 2000.

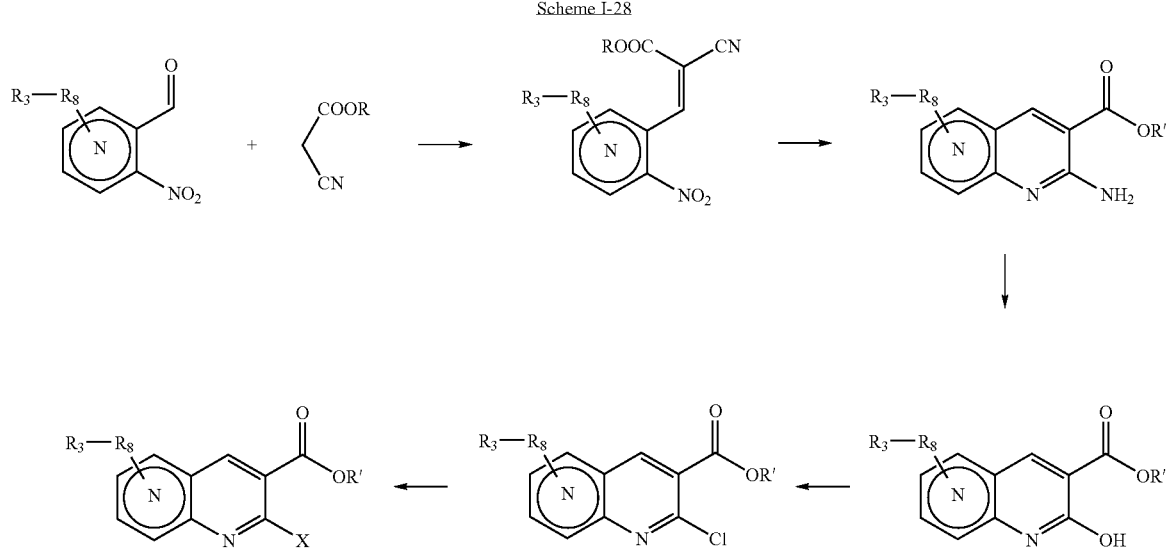

Scheme I-28

X=$R^5$, where $R^5$=$OR^{24}$, $NR^{10}R^{24}$, $SR^{24}$, H

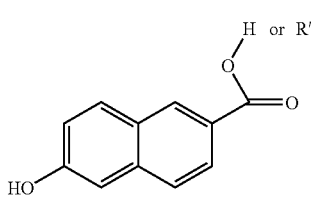

The following references contain preparations or references to preparations of the quinoline acid above. The hydroxy group may be derivatized to an ether or converted to a triflate which may be converted to cyano using palladium/copper catalyzed couplings or the triflate may be coupled directly to heterocyclic or aromatic stannanes.

References for above:
Yabe et. al. JP 10087489A2
Yabe et. al. PCT WO9628423
Portlock et. al U.S. Pat. No. 4,461,896A
Wright et. al. DE3004370

Scheme I-29 shows the preparation of glyoxylic acid chloride derivatives which are also useful intermediates for the preparation of compounds of Formula I. The glyoxylic

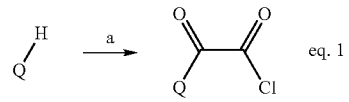

Scheme I-29 eq. 1

An alternate method (three step procedure) for preparing compounds of Formula I is shown in Scheme I30, below. Reaction of a known or synthesized heterocyclic acetic acid derivative of Formula XYZ1 with a piperazine derivative of Formula IV, under standard peptide coupling conditions will afford the desired amides of Formula Im. Preferred peptide coupling conditions include the use of EDC in the presence of diisopropylethylamine. Treatment of the amide derivative, Ie, with a strong base, such as lithium diisopropylamide (LDA), followed by quenching with (+,-)-Davis' reagent will afford the corresponding α-hydroxyamide derivatives of formula If. Finally, oxidation of the α-hydroxyamide of Formula If, with an oxidant, such as Dess-Martin reagent, will provide the desired α-ketoamides of formula Ib.

An alternative route which may be used to obtain the (α-ketoamides of Formula Ib involves the direct oxidation of the acetamide derivative of Formula Im. A preferred method is to treat the acetamide derivative of Formula Ie with an oxidant, such as selenium dioxide (SeO$_2$) in a polar solvent such as dioxane to provide the desired α-ketoamides of formula Ib.

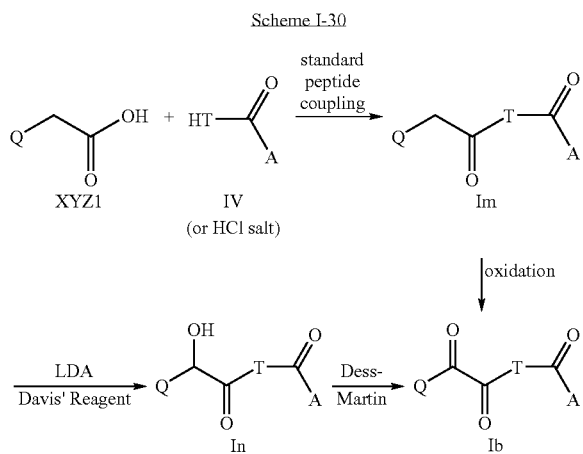

Scheme I-30

It will be appreciated by one skilled in the art that certain functional groups present on the heterocyclic moiety represented by the variable Q of a compound of Formula I or its precursor may be converted to other groups by transformations known in the art. Schemes 6–9 provide nonlimiting examples of transformations useful to provide various compounds of Formula I. In Schemes 6–9 various functional group transformations are shown for substituents of the heterocyclic moiety represented by Q in the general formula (with the point of attachment being at one of positions $R^1$–$R^8$). In these schemes, Q' represents the portion of Q which together with the indicated substituent makes up Q. It is to be understood that the functional group conversions may be applicable to any of the $R^1$–$R^8$ positions of the heterocyclic moiety (other than the $R^1$–$R^8$ position which is the point of attachment). The transformations depicted in Schemes 6–9 are applicable to both intermediates which can then be converted to compounds of Formula I and to compounds of Formula I.

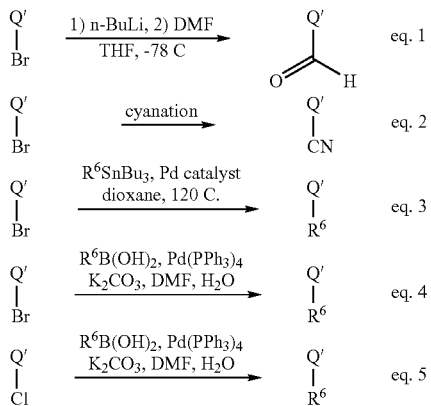

Scheme 6
Conversion of halides:

Scheme 6, above, depicts the conversion of a bromide to various other functional groups. In equation 1, treatment of the bromide with a strong base, such as n-butyl lithium, in an aprotic solvent, such as THF, followed by treatment with dimethylformamide results in the aldehyde shown.

Equation 2 of Scheme 6 depicts the conversion of the bromide to the cyano derivative. This transformation can be achieved by treating the bromide with a reagent such as sodium cyanide, copper cyanide or zinc cyanide in a solvent such as dimethylformamide.

Equations 3 and 4 of Scheme 6 show a suitable bromo derivative may undergo metal mediated couplings with various stannanes or boronic acid derivatives. Conditions for the Stille-type coupling, shown in equation 3, are well known in the art and involve treatment of the bromide (or iodide or triflate) with an aryl, heteroaryl or vinyl stannane in the presence of an appropriate palladium catalyst in an appropriate solvent. Palladium catalysts used include, but are not limited to, tetrakis-triphenylphosphine palladium and palladium (II) acetate. Appropriate solvents include, but are not limited to, polar solvents such as dioxane and 1-methyl-2-pyrrolidinone. Numerous examples of conditions for carrying out the Stille reaction may be found in references such as Farina, V.; Roth G. P.; *Adv. Met.-Org. Chem.* 1996, 5, 1–53; Farina, V.; Krishnamurthy, V.; Scott, W. J.; *Org. React.* (N.Y.) 1997, 50, 1–652; and Stille, J. K.; *Angew. Chem. Int. Ed. Engl.* 1986, 25, 508–524.

Equation 4 of Scheme 6 depicts the Suzuki-type coupling of the bromide with an appropriate boronic acid derivative. Appropriate boronic acid derivatives include aryl and heteroaryl boronic acid derivatives. This transformation may be carried out in the presence of an appropriate palladium catalyst, such as tetrakis-triphenylphosphine palladium, and a base, such as potassium carbonate, in a solvent or solvent mixture such as dimethylformamide and water. Typical reaction conditions for carrying out the Suzuki-type reaction can be found in Miyaura, N.; Suzuki, A.; *Chem. Rev.* 1995, 95, 2457.

Alternative methods are available to one skilled in the art for carrying out transformations analogous to those shown in equations 3 and 4 of Scheme 6. For example, substituted azabenzoxazoles or other heterocyclic groups of general formula Q containing a chloride, bromide, iodide, triflate, or phosphonate undergo coupling reactions with a boronate (Suzuki type reactions) or a stannane to provide the corresponding substituted heterocycles. Triflates and boronates are prepared via standard literature procedures from the corresponding hydroxy bearing heterocycle. The substituted heterocyles may undergo metal mediated coupling to provide compounds of Formula I wherein the desired substituent is aryl, heteroaryl, or heteroalicyclic for example. The bromoheterocycle intermediates, (or heterocyclic triflates or iodides) may undergo Stille-type coupling with heteroarylstannanes as shown in equation 3. Conditions for this reaction are well known in the art and the following are three example references a) Farina, V.; Roth, G. P. Recent advances in the Stille reaction; *Adv. Met.-Org. Chem.* 1996, 5, 1–53. b) Farina, V.; Krishnamurthy, V.; Scott, W. J. The Stille reaction; *Org. React.* (N.Y.) 1997, 50, 1–652. and c) Stille, J. K. *Angew. Chem. Int. Ed. Engl.* 1986, 25, 508–524. Other references for general coupling conditions are also in the reference by Richard C. Larock Comprehensive Organic Transformations 2nd Ed. 1999, John Wiley and Sons New York. All of these references provide numerous conditions at the disposal of those skilled in the art to carry out transformations such as those depicted in equation 3 and 4 of Scheme 6. It can be well recognized that a heterocyclic stannane could also be coupled to a heterocyclic or aryl halide or triflate to construct compounds of Formula I.

Suzuki coupling (Norio Miyaura and Akiro Suzuki *Chem Rev.* 1995, 95, 2457.) between a bromo heterocycle intermediate and a suitable boronate could also be employed.

Suzuki couplings between chloroheterocycle intermediates, as depicted in equation 5 of Scheme 6, are also feasible. If standard conditions fail new specialized catalysts and conditions can be employed. Some references (and the references therein) describing catalysts which are useful for coupling with aryl and heteroaryl chlorides are: Littke, A. F.; Dai, C.; Fu, G. C. *J. Am. Chem. Soc.* 2000, 122(17), 4020–4028; Varma, R. S.; Naicker, K. P. *Tetrahedron Lett.* 1999, 40(3), 439–442; Wallow, T. I.; Novak, B. M. *J. Org. Chem.* 1994, 59(17), 5034–7; Buchwald, S.; Old, D. W.; Wolfe, J. P.; Palucki, M.; Kamikawa, K.; Chieffi, A.; Sadighi, J. P.; Singer, R. A.; Ahman, J PCT Int. Appl. WO 0002887 2000; Wolfe, J. P.; Buchwald, S. L. *Angew. Chem., Int. Ed.* 1999, 38(23), 3415; Wolfe, J. P.; Singer, R. A.; Yang, B. H.; Buchwald, S. L. *J. Am. Chem. Soc.* 1999, 121(41), 9550–9561; Wolfe, J. P.; Buchwald, S. L. *Angew. Chem., Int. Ed.* 1999, 38(16), 2413–2416; Bracher, F.; Hildebrand, D.; *Liebigs Ann. Chem.* 1992, 12, 1315–1319; and Bracher, F.; Hildebrand, D.; *Liebigs Ann. Chem.* 1993, 8, 837–839.

Alternatively, the boronate or stannane may be formed on the heterocyclic moiety via methods known in the art and the coupling performed in the reverse manner with aryl or heteroaryl based halogens or triflates.

Methods for direct addition of aryl or heteroaryl organometallic reagents to alpha chloro nitrogen containing heterocyles or the N-oxides of nitrogen containing heterocycles are known and applicable to the compounds described herein. Some examples are Shiotani et. al. *J. Heterocyclic Chem.* 1997, 34(3), 901–907; Fourmigue et.al. *J.Org. Chem.* 1991, 56(16), 4858–4864.

Scheme 7, below, depicts various transformations of a carboxylic acid group with the $R^6$ position being used for illustrative purposes. In equation 1, the carboxylic acid group is being converted to an amide by using standard peptide coupling techniques. Standard peptide coupling refers to coupling an amine with a carboxylic acid in the presence of an amine acid coupling reagent such as DCC, PyBop, EDC, or DEPBT.

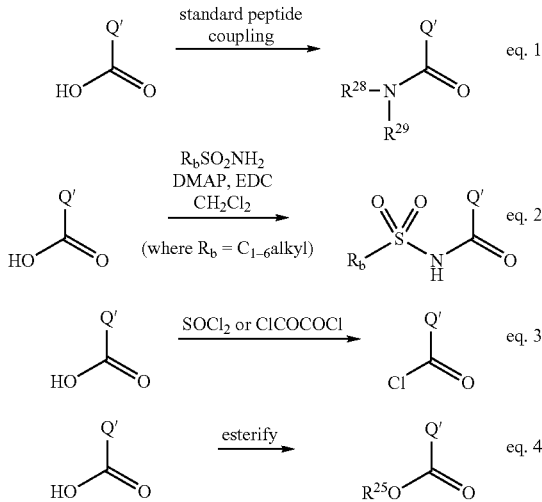

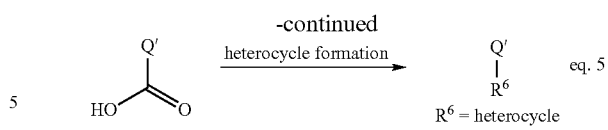

Equation 2 of Scheme 7 shows the conversion of the carboxylic acid group to an acylsulfonamide group by treating the carboxylic acid with a primary sulfonamide, such as methylsulfonamide or phenylsulfonamide in the presence of a peptide coupling agent, such as EDC, and a base, such as DMAP, in an appropriate aprotic solvent, such as dichloromethane.

The carboxylic acid group can also be converted to the corresponding acid chloride by treatment with thionyl chloride (neat or in an inert solvent) or oxalyl chloride in an inert solvent such as benzene, toluene, THF or dichloromethane as shown in equation 3 of Scheme 7. The acid chloride may then be further reacted, for example with an excess of ammonia, primary amine or secondary amine in an inert solvent such as benzene, toluene, THF or dichloromethane to provide the corresponding amides. The acid chloride may also be reacted with a stoichiometric amount of amine in the presence of a base, such as triethylamine, 4-methylmorpholine, 2,6-lutidine or pyridine. Alternatively, the acid chloride may be reacted with an amine under basic conditions (usually sodium hydroxide or potassium hydroxide) in solvent mixtures containing water and possibly a miscible cosolvent such as dioxane or THF.

The carboxylic acid group can also be esterified, as shown in equation 4 of Scheme 7, using standard conditions well known in the art. For example, the acid may be converted to the methyl ester by treatment with diazomethane or trimethylsilyldiazomethane in methanol/benzene. Other standard esterification conditions, such as those described by Richard C. Larock in Comprehensive Organic Transformations $2^{nd}$ Ed. 1999, John Wiley and Sons, New York or Theodora W. Greene and Peter G. M. Wuts in Protective Groups in Organic Synthesis $3^{rd}$ Ed. 1999, Wiley, New York may also be used.

Equation 5 of Scheme 7 shows the acid being used as a versatile precursor for the formation of various heterocycles. The acid could be converted to hydrazonyl bromide and then a pyrazole via methods described by Shawali in *J. Heterocyclic Chem.* 1976, 13, 989. One method for general heterocycle synthesis would be to convert the acid to an alpha bromo ketone by conversion to the acid chloride using standard methods, reaction with diazomethane, and finally reaction with HBr. The alpha bromo ketone could be used to prepare many different compounds of Formula I as it can be converted to many heterocycles or other compounds of Formula I. Alpha amino ketones can be prepared by displacement of the bromide with amines. Alternatively, the alpha bromo ketone could be used to prepare heterocycles not available directly from the aldeheyde or acid. For example, using the conditions described by Hulton et al. in *Synth. Comm.* 1979, 9, 789 to react the alpha bromo ketone would provide oxazoles. Reaction of the alpha bromoketone with urea via the methods described by Pattanayak, B. K. et al. in *Indian J. Chem.* 1978, 16, 1030 would provide 2-amino oxazoles. The alpha bromoketone could also be used to generate furans using beta keto esters as described in *Chemische Berichte* 1902, 35, 1545 and *Chemische Bericte* 1911, 44, 493; pyrroles (from beta dicarbonyls as in *Indian J. Chem.* 1973, 11, 1260; thiazoles by Hantsch methods as described by Roomi et al in *Can. J. Chem.* 1970, 48, 1689;

or isoxazoles and imidazoles as described by Sorrel, T. N. in *J. Org. Chem.* 1994, 59, 1589. Coupling of the aforementioned acid chloride with N-methyl-O-methyl hydroxyl amine would provide a "Weinreb Amide" which could be used to react with alkyl lithiums or Grignard reagents to generate ketones. Reaction of the Weinreb anion with a dianion of a hydroxyl amine would generate isoxazoles as in Nitz, T. J. et al. *J. Org. Chem.* 1994, 59, 5828–5832. Reaction with an acetylenic lithium or other carbanion would generate alkynyl indole ketones. Reaction of this alkynyl intermediate with diazomethane or other diazo compounds would give pyrazoles as in Bowden, K. et al. *J. Chem. Soc.* 1946, 953. Reaction with azide or hydroxyl amine would give heterocycles after elimination of water. Nitrile oxides would react with the alkynyl ketone to give isoxazoles as described in Chimichi, *S. Synth. Comm.* 1992, 22, 2909. Reaction of the initial acid to provide an acid chloride using for example oxalyl chloride or thionyl chloride or triphenyl phosphine/carbon tetrachloride provides a useful intermediate as noted above. Reaction of the acid chloride with an alpha ester substituted isocyanide and base would give 2-substituted oxazoles as described by Scholkopf et al. in *Angew. Int. Ed. Engl.* 1971, 10(5), 333. These could be converted to amines, alcohols, or halides using standard reductions or Hoffman/Curtius type rearrangements.

Equation 1 of Scheme 8 depicts the oxidation of an heterocyclic aldehyde to the corresponding carboxylic acid. Numerous methods are suitable for the conversion of an aldehyde to an acid and many of these are well known in the art and described in standard organic chemistry texts such as Richard C. Larock in Comprehensive Organic Transformations 2nd Ed. 1999, John Wiley and Sons, New York. One preferred method is the use of silver nitrate or silver oxide in aqueous or anhydrous methanol at a temperature of about 25° C. or as high as reflux for 1 to 48 hours. Alternatively, the aldehyde could be oxidized to the acid using other standard oxidants such as $KMnO_4$ or $CrO_3/H_2SO_4$.

Equation 2 of Scheme 8 depicts the reaction of the aldehyde with hydroxylamine (R=H) in a suitable solvent, such as ethanol to provide the oximes shown.

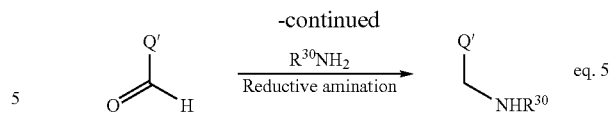

Equation 3 of Scheme 8 shows the conversion of the aldehyde group to an oxazole by using TOSMIC in the presence of potassium carbonate in methanol. The aldehyde could also be reacted with a metal reagent ($R^{25}M$) or Grignard reagent ($R^{25}MgX$, X=halide) to generate secondary alcohols which could then be oxidized to the corresponding ketones as shown in equation 4 of Scheme 8. Suitable Grignard reagents would include reagents wherein $R^{25}$ is alkyl, aryl or heteroaryl. The oxidation of the secondary alcohols to the corresponding ketones, shown as the second step in equation 4, may be accomplished using oxidants such as TPAP, $MnO_2$ or PCC.

Scheme 9

Conversion of nitriles:

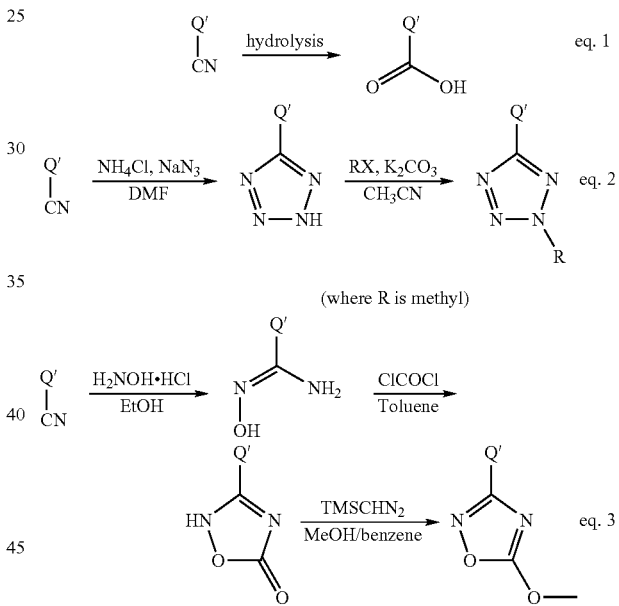

Equation 1 of Scheme 9 depicts the hydrolysis of a nitrile group to the corresponding carboxylic acid. Suitable conditions for carrying out this hydrolysis employ heating the nitrile at reflux with potassium hydroxide in a mixture of water and ethanol for 1 to 100 hours to provide the acid.

Equation 2 of Scheme 9 depicts the conversion of the nitrile to a tetrazole by reacting the nitrile with ammonium chloride and sodium azide in DMF. The tetrazole can then be alkylated by treatment with an electrophile, such as an alkyl halide in the presence of potassium carbonate or alternatively by treatment with a reagent such as trimethylsilyldiazomethane in methanol/benzene.

Scheme 9, equation 3 shows the preparation of an oxadiazole from the nitrile by the addition of hydroxylamine followed by ring closure upon treatment with phosgene. The oxadiazole may then be methylated using trimethylsilyldiazomethane ($TMSCHN_2$) in a mixture of methanol and benzene.

Scheme 8

Conversion of aldehydes:

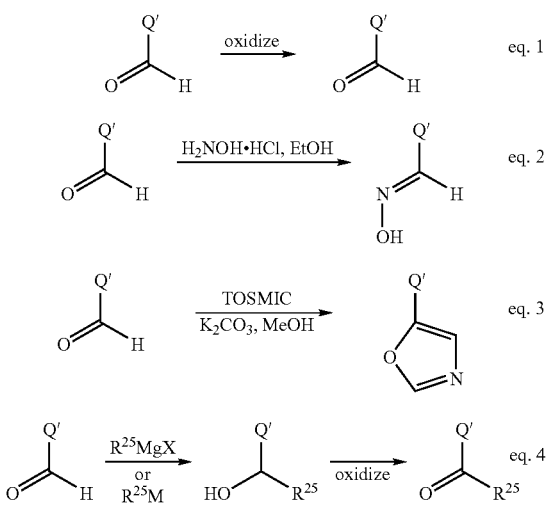

Experimental Procedures

The following examples represent typical syntheses of the compounds of Formula I as described generally above. These examples are illustrative only and are not intended to limit the invention in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040–0.063 particle size; EM Science supply). $^1$H NMR spectra were recorded on Bruker DRX-500f at 500 MHz (or Bruker DPX-300B or Varian Gemini 300 at 300 MHz as stated). The chemical shifts were reported in ppm on the δ scale relative to δ TMS=0. The following internal references were used for the residual protons in the following solvents: $CDCl_3$ ($δ_H$ 7.26), $CD_3OD$ ($δ_H$ 3.30), and DMSO-d6 ($δ_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

| LC/MS Method (i.e., compound identification) | |
|---|---|
| Column A: | YMC ODS-A S7 3.0 × 50 mm column |
| Column B: | PHX-LUNA C18 4.6 × 30 mm Column |
| Column C: | XTERRA ms C18 4.6 × 30 mm column |
| Column D: | YMC ODS-A C18 4.6 × 30 mm column |
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Column H: | YMC C18 S5 4.6 × 33 mm column |
| Column I: | YMC ODS-A C18 S7 3.0 × 50 mm column |
| Column J: | Xterra MS C18 5 um 4.6 × 30 mm column |
| Gradient: | 100% Solvent A/0% Solvent B to 0% Solvent A/100% Solvent B |
| Gradient time: | 2 minutes |
| Hold time: | 1 minute |
| Flow rate: | 5 mL/min |
| Detector Wavelength: | 220 nm |
| Solvent A: | 10% MeOH/90% $H_2O$/0.1% Trifluoroacetic Acid |
| Solvent B: | 10% $H_2O$/90% MeOH/0.1% Trifluoroacetic Acid |

Compounds purified by preparative HPLC were diluted in methanol (1.2 mL) and purified using the following methods on a Shimadzu LC-10A automated preparative HPLC system.

Preparative HPLC Method (i.e., Compound Purification)

Purification Method: Initial gradient (40% B, 60% A) ramp to final gradient (100% B, 0% A) over 20 minutes, hold for 3 minutes (100% B, 0% A)

| Solvent A: | 10% MeOH/90% $H_2O$/0.1% Trifluoroacetic Acid |
|---|---|
| Solvent B: | 10% $H_2O$/90% MeOH/0.1% Trifluoroacetic Acid |
| Column: | YMC C18 S5 20 × 100 mm column |
| Detector Wavelength: | 220 nm |

Preparation of Intermediates is Described Below with Characterization Data Provided in Tables 1A–1E

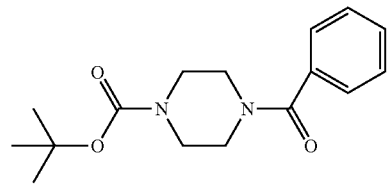

Preparation 1

To a solution of tert-butyl-1-piperazinecarboxylate (15.0 g. 80.5 mmol) and benzoic acid (8.94 g, 73.2 mmol) in $CH_2Cl_2$ (500 mL), was added DMAP (9.84 g, 80.5 mmol) and EDC (15.39 g, 80.5 mmol). The reaction mixture was stirred at rt for 17 h, and then washed with excess hydrochloric acid (5×250 mL, 1 N aq.) and water (350 mL). The organic layer was dried over $MgSO_4$, filtered and the filtrate concentrated in vacuo to provide Preparation 1 as an off white solid (21 g, 99%). $^1$H NMR: (300 MHz, $CD_3OD$) δ7.46 (m, 5H), 3.80–3.30 (b m, 8H), 1.47 (s, 9H); LC/MS: (ES+) m/z (M+H) $^+$=291, (2M+H)$^+$=581, HPLC $R_f$=1.430.

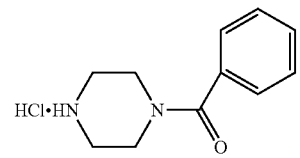

Preparation 2

To Preparation 1 was charged a solution of HCl in Dioxane (80 mL, 4 M), and the mixture stirred at room temperature for 5 h. The reaction mixture was concentrated in vacuo to afford the hydrochloride salt of Preparation 2 as a white solid (100% conversion). $^1$H NMR: (300 MHz, $CD_3OD$) δ7.5 (m, 5H), 4.0–3.7 (b, 4H), 3.7–3.6 (b m, 4H); LC/MS: (ES+) m/z (M+H)$^+$=191, (2M+H)$^+$=381, HPLC $R_f$=0.210.

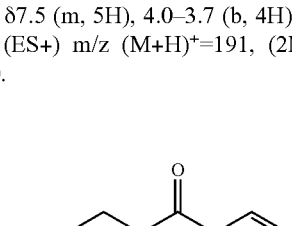

Preparation 3

Prepared in the same manner as Preparations 1 and 2 starting from tert-butyl-1-(2-(R)-methylpiperazine)carboxylate (15.0 g. 80.5 mmol) and benzoic acid (8.94 g, 73.2 mmol). $^1$H NMR: (300 MHz, $CD_3OD$) δ7.47 (m, 5H), 4.50 (app d, J=10.6, 1H), 3.59 (b s, 1H), 3.14–2.57(b m, 5H), 1.15–0.97 (b m, 3H); LC/MS: (ES+) m/z (M+H)$^+$=205, (2M+H)$^+$=409, HPLC $R_f$=0.310.

Preparations 4–5

Preparations 4 and 5 were prepared according to the following general procedure and as further described below.

General Procedures:

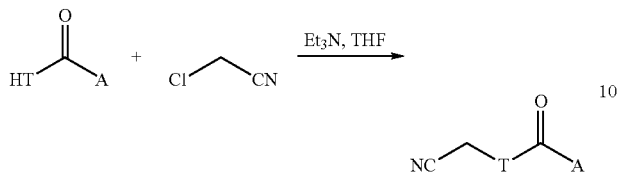

Typical procedure to prepare 1-carbonyl-4-cyanomethylpiperazine derivatives: An excess of chloroacetonitrile (7 mL) was added to a solution of piperazine derivative of formula HTC(O)A (10.5 mmol) in THF (100 mL) and $Et_3N$ (10 mL). The reaction was stirred for 10 hours then was quenched with saturated aqueous $NaHCO_3$ (100 mL). The aqueous phase was extracted with EtOAc (3×100 mL). The combined organic layer was dried over $MgSO_4$, filtered, and the filtrate concentrated to a residue, which was used in the further reactions without any purification.

Preparation 4

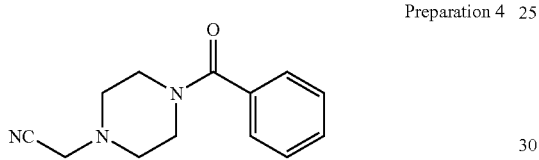

An excess of chloroacetonitrile (7 mL) was added in to a solution of 1-benzoylpiperazine (2 g, 10.5 mmol) in THF (100 mL) and $Et_3N$ (10 mL). The reaction was stirred for 10 h before being quenched with saturated aqueous $NaHCO_3$ (100 mL). The aqueous phase was extracted with EtOAc (3×100 mL). The combined organic layer was dried over $MgSO_4$ and concentrated to a residue, Preparation 4, which was used in the further reactions without any purification.

Characterization of Compounds which were Prepared via the Same Method Described above Shown in Table 1A:

Preparation 5

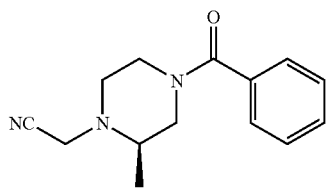

An excess of chloroacetonitrile (7 mL) was added in to a solution of 1-benzoyl-3-(R)-piperazine (2 g, 10.5 mmol) in THF (100 mL) and $Et_3N$ (10 mL). The reaction was stirred for 10 h before being quenched with saturated aqueous $NaHCO_3$ (100 mL). The aqueous phase was extracted with EtOAc (3×100 mL). The combined organic layer was dried over $MgSO_4$ and concentrated to a residue, Preparation 5, which was used in the further reactions without any purification.

Preparation of Quinoline N-Oxide:

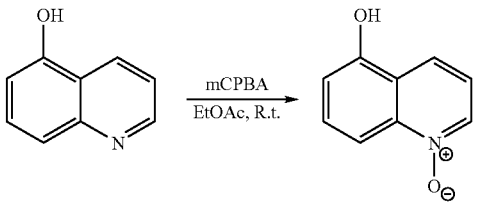

Typical procedure to prepare quinoline N-oxide from quinoline: Preparation of 5-hydroxylquinoline N-oxide: mCPBA (172 mg) was added into a solution of 5-hydroxylquinoline (72.6 mg) in EtOAc (10 ml) at room temperature. After the reaction was stirred at room temperature for 12 hours, a precipitate was formed and collected through filtration to afford 77.5 mg of 5-hydroxylquinoline N-oxide. MS m/z: $(M+H)^+$ calcd for $C_9H_8NO_2$ 162.06, found 162.02. HPLC retention time: 0.69 minutes (column I).

TABLE 1A

| Entry # | Structure | MS $(M + H)^+$ Calcd. | MS $(M + H)^+$ Observ. And Retention Time |
|---|---|---|---|
| Preparation 4 | 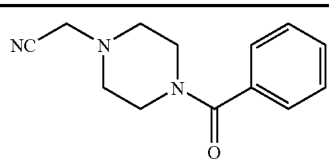 | 230.13 | 230.02<br>0.84 min<br>(column I) |
| Preparation 5 | 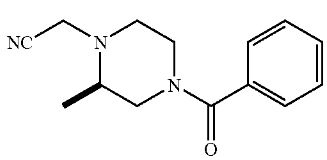 | 244.14 | 244.09<br>0.96 min<br>(column I) |
| Preparation 5a (same method as Prep 4 and 5) | 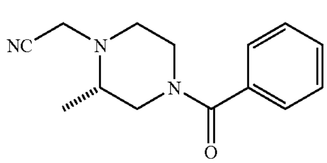 | 244.14 | 244.09<br>0.95 min<br>(column I) |

Characterization of Compounds which were Prepared via the Same Method Described above Shown in Table 1B:

TABLE 1B

| Entry # | Structure | MS (M + H)+ Calcd. | MS (M + H)+ Observ. And Retention Time |
|---|---|---|---|
| NO-01 | Br-quinoline N-oxide | 223.97 | 223.85 1.07 min (column I) |
| NO-02 | HO-quinoline N-oxide | 162.06 | 162.02 0.56 min (column I) |

Preparation of Quinoline Nitrile from N-Oxide:

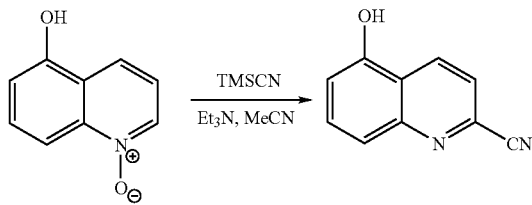

Typical procedure to prepare 2-cyanoquinoline from N-oxide: Preparation of 2-cyano-5-hydroxyl-2-quinoline: Trimethylsilyl cyanide (12.4 ml) was added into a solution of 5-hydroxyl-quinoline N-oxide (5 g) with triethylamine (13 ml) in MeCN. After the reaction was stirred at room temperature for 12 hours, solvents were removed under vaccum to provide a residue which was then partitioned between saturated NaHCO$_3$ solution (100 ml) and EtOAc (100 ml). The aqueous solution was then extracted with EtOAc (2×100 ml). And the combined organic layer was dried over anhydrous MgSO$_4$, filtered and concentrated to afford a crude product which purified by silica gel column chromatography to provide 5.3 g of 2-cyano-5-hydroxylquinoline. MS m/z: (M+H)+ calcd for C$_{10}$H$_7$N$_2$O 171.06, found 171.03. HPLC retention time: 1.22 minutes (column I).

Characterization of Compounds which were Prepared via the Same Method Described above Shown in Table 1C:

TABLE 1C

| Entry # | Structure | MS (M + H)+ Calcd. | MS (M + H)+ Observ. And Retention Time |
|---|---|---|---|
| CN-01 | MeO-quinoline-CN | 185.07 | 184.92 1.39 min (column I) |
| CN-02 | HO-quinoline-CN | 171.06 | 171.03 1.17 min (column I) |
| CN-03 | Br-quinoline-CN | 232.97 | 232.92 1.52 min (column I) |

Preparation of Quinoline Acid via Hydrolysis of Nitrile:

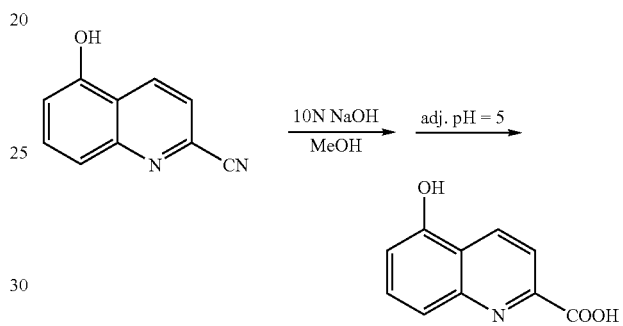

Typical procedure to prepare quinoline acid from nitrile: Preparation of 5-hydroxyl-2-quinoline carboxylic acid: 2-cyano-5-hydroxylquinoline (5 g) was added into a mixed solution of 10N NaOH (150 ml) and MeOH (400 ml). After heated at 100° C. for two hours, MeOH was removed under vaccum to give an aqueous solution. When the pH of the solution was adjusted to 5 by using 10N HCl, a yellow solid precipitated out from the solution to afford 4.61 g of 5-hydroxyl-2-quinoline carboxylic acid. MS m/z: (M+H)+ calcd for C$_{10}$H$_8$NO$_3$ 190.05, found 190.03. HPLC retention time: 0.56 minutes (column I)

Preparation of Quinoline Acid via Oxidation of Methyl Group:

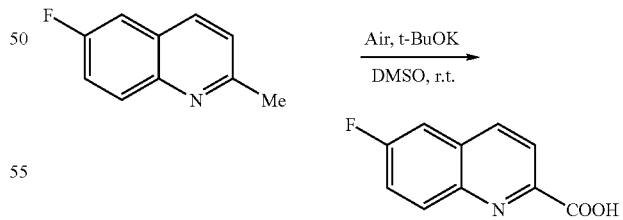

Typical procedure to prepare quinoline carboxylic acid via oxidation: Preparation of 6-fluoro-2-quinoline carboxylic acid: Air was bubbled into a solution of 6-fluoro-2-methylquinoline (1 g) with an excess of t-BuOK (20 ml, 1.0M in t-BuOH) in DMSO. When solvents were almost all evaporated, water (20 ml) was added to the residue and pH was adjusted to 7 by adding 10N HCl solution. The aqueous solution was then extracted with EtOAc (3×20 ml). And the combined organic layer was dried over anhydrous MgSO$_4$, filtered and concentrated to afford a crude product which purified by silica gel column chromatography to provide 1.18 g of 6-fluoro-2-quinoline carboxylic acid. MS m/z: $(M+H)^+$ calcd for $C_{10}H_7FNO_2$ 192.05, found 192.04. HPLC retention time: 1.04 minutes (column I).

Characterization of Compounds which were Prepared via the Same Methods Described above Shown in Table 1D:

TABLE 1D

| Entry # | Structure | MS $(M + H)^+$ Calcd. | MS $(M + H)^+$ Observ. And Retention Time |
|---|---|---|---|
| Acid-01 | MeO-quinoline-COOH | 204.07 | 204.03 0.91 min (column I) |
| Acid-02 | Br-quinoline-COOH | 251.97 | 251.92 1.32 min (column I) |
| Acid-03 | HO-quinoline-COOH | 190.05 | 190.01 0.45 min (column I) |

Preparation of Quinoline Ester from Acid:

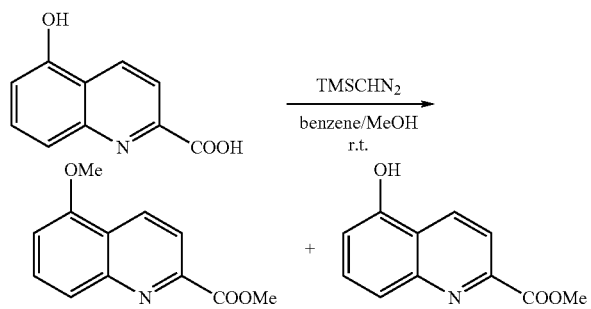

Typical procedure to prepare quinoline ester from acid: Preparation of methyl 5-hydroxyl-2-quinoline carboxylate and methyl 5-methoxy-2-quinoline carboxylate: Trimethylsilyldiazomethane (0.61 ml, 2.0M in hexane) was added into a solution of 5-hydroxyl-2-quinoline carboxylic acid (100 ml) in benzene (5 ml) and MeOH (5 ml). After two hours, solvents were removed under vaccum to give a residue, which was partitioned between saturated NaHCO3 (10 ml) and EtOAc (10 ml). The aqueous layer was further extracted with EtOAc (2×10 ml). The combined organic layer was dried over anhydrous MgSO₄, filtered and concentrated to afford a mixture of two products which purified by silica gel thin layer chromatography to provide 31.4 mg of methyl 5-hydroxyl-2-quinoline carboxylate [MS m/z: $(M+Na)^+$ calcd for $C_{11}H_9NNaO_3$ 226.05, found 225.99. HPLC retention time: 1.19 minutes (column I)] and 24.9 mg of methyl 5-methoxy-2-quinoline carboxylate [MS m/z: $(M+Na)^+$ calcd for $C_{12}H_{11}NNaO_3$ 240.06, found 239.98. HPLC retention time: 1.51 minutes (column I)].

Characterization of Compounds which were Prepared via the Same Method Described above Shown in Table 1E:

TABLE 1E

| Entry # | Structure | MS $(M + H)^+$ Calcd. | MS $(M + H)^+$ Observ. And Retention Time |
|---|---|---|---|
| Ester-01 | MeO-quinoline-COOMe | 218.08 | 218.01 1.91 min (column I) |
| Ester-02 | HO-quinoline-COOMe | 204.07 | 204.00 1.07 min (column I) |
| Ester-03 | F-quinoline-COOMe | 228.04 $(M + Na)^+$ | 227.97 $(M + Na)^+$ 1.41 min (column I) |
| Ester-04 | Br-quinoline-COOMe | 265.98 | 265.94 1.57 min (column I) |

Typical Procedures and Characterization of Selected Examples of Compounds of Formula I with Characterization Data Provided in Tables 2–6 and Biological Data Provided in Tables 7–9:

General Procedures in Scheme 1:

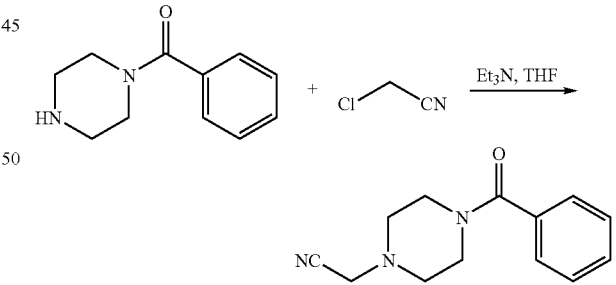

Typical procedure to prepare intermediate 1-benzyl-4-cyanomethylpiperazines: Preparation of 1-benzyl-4-cyanomethylpiperazine: An excess of chloroacetonitrile (7 ml) was added in to a solution of benzylpiperazine (2 g, 10.5 mmol) in THF (100 ml) and Et₃N (10 ml). The reaction was stirred for 10 hours before quenched with saturated aqueous NaHCO₃ (100 ml). The aqueous phase was extracted with EtOAc (3×100 ml). The combined organic layer was dried over MgSO₄ and concentrated to a residue, which was used in the further reactions without any purification.

Characterization of Intermediate Compounds which were Prepared via the same Method Described above Shown in Table 2A:

TABLE 2A

| Entry # | Structure | MS (M + H)+ Calcd. | MS (M + H)+ Observ. And Retention Time |
|---|---|---|---|
| SM-01 | 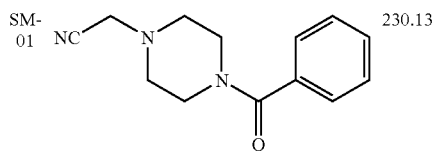 | 230.13 | 230.02<br>0.84 min<br>(column I) |
| SM-02 | 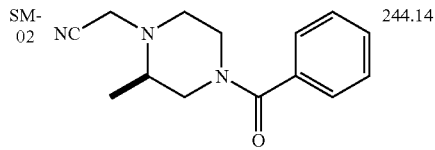 | 244.14 | 244.09<br>0.96 min<br>(column I) |
| SM-03 | 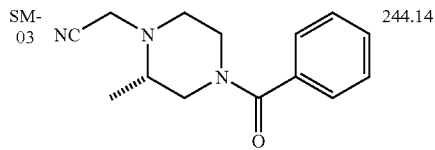 | 244.14 | 244.09<br>0.95 min<br>(column I) |

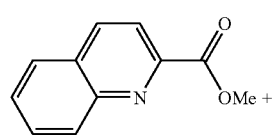

+

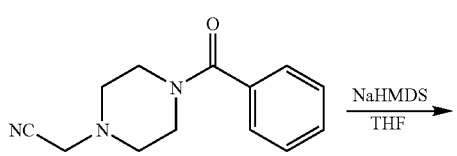

$\xrightarrow{\text{NaHMDS}}$ THF

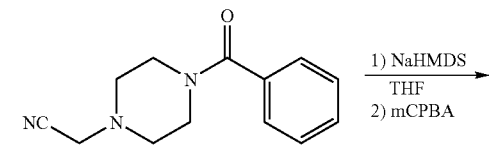

Typical procedure to prepare final Compound I, cyanoketone: Preparation of N-(benzoyl)-N'-[2-(quinolin-2-yl)-2-oxo-1-cyano-ethyl]-piperazine: NaHMDS (1.75 ml, 1M in THF) was added into a solution of 1-benzyl-4-cyanomethylpiperazin (100 mg) and methyl quinoline-2-carboxylate (82 mg) in THF. The reaction was stirred for 10 hours. After solvents were removed under vaccum, the residue was purified using Shimadzu automated preparative HPLC System to give N-(benzoyl)-N'-[2-(quinolin-2-yl)-2-oxo-1-cyano-ethyl]-piperazine (10 mg).

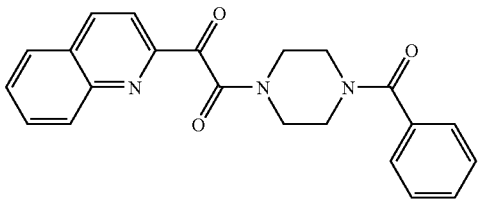

1) NaHMDS THF
2) mCPBA

Typical procedure to prepare final Compound I, oxoacetylpiperazines: Preparation of N-(benzoyl)-N'-[(quinolin-2-yl)-2-oxoacetyl]-piperazine: NaHMDS (1.75 ml, 1M in THF) was added into a solution of 1-benzyl-4-cyanomethylpiperazin (100 mg) and methyl quinoline-2-carboxylate (82 mg) in THF. After the reaction was stirred for 10 hours, mCPBA (200 mg, >77%) was added and the resulted mixture was stirred for another 10 hours. Then solvents were removed under vaccum, the residue was purified using Shimadzu automated preparative HPLC System to give N-(benzoyl)-N'-[(quinolin-2-yl)-2-oxoacetyl]-piperazine (1.4 mg).

TABLE 2

Characterization of Compounds of Formula I with the Following Substructure:

| Entry # | Q | R | MS (M + H)+ Calcd. | MS (M + H)+ Observ. And Retention Time |
|---|---|---|---|---|
| 16 | quinolin-2-yl | H | 385.17 | 385.19 1.42 min. (Column A) |
| 15 | quinolin-2-yl | Me | 399.18 | 399.10 1.44 min. (Column A) |
| 18 | quinolin-2-yl | (R)-Me | 399.18 | 399.09 1.45 min. (Column A) |
| 21 | quinolin-2-yl | (S)-Me | 399.18 | 399.08 1.45 min. (Column A) |
| 17 | isoquinolin-3-yl | H | 385.17 | 385.09 1.22 min. (Column A) |
| 19 | quinoxalin-2-yl | (R)-Me | 400.18 | 400.07 1.43 min. (Column A) |
| 23 | quinoxalin-2-yl | (S)-Me | 400.18 | 400.08 1.42 min. (Column A) |
| 40 | 1,6-naphthyridin-2-yl | H | 386.16 | 386.09 1.20 min (Column I) |

TABLE 2-continued

Characterization of Compounds of Formula I with the Following Substructure:

| Entry # | Q | R | MS (M + H)+ Calcd. | MS (M + H)+ Observ. And Retention Time |
|---|---|---|---|---|
| 20 | 1,6-naphthyridin-2-yl | (R)-Me | 400.18 | 400.09 1.11 min. (Column A) |
| 22 | 1,6-naphthyridin-2-yl | (S)-Me | 400.18 | 400.09 1.11 min. (Column A) |
| 24 | 5,8-difluoro-4-(phenylthio)quinolin-3-yl | H | 529.15 | 528.96 1.01 min. (column A) |
| 26 | 6-hydroxyquinolin-2-yl | Me | 415.18 | 415.05 1.50 min (column I) |
| 25 | 6-bromoquinolin-2-yl | Me | 477.09 | 476.87 1.85 min (column I) |
| 29 | 6-methoxyquinolin-2-yl | Me | 429.19 | 429.25 1.58 min (column I) |
| 27 | 4-hydroxy-6-(trifluoromethoxy)quinolin-3-yl | Me | 499.16 | 499.26 1.181 min (column I) |

TABLE 2-continued

Characterization of Compounds of Formula I with the Following Substructure:

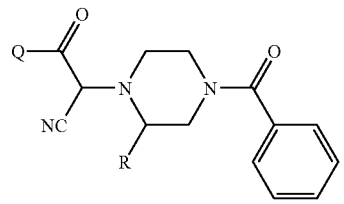

| Entry # | Q | R | MS (M + H)+ Calcd. | MS (M + H)+ Observ. And Retention Time |
|---|---|---|---|---|
| 40 | 6-Br-naphthalen-2-yl | (R)-Me | 476.10 | 476.00<br>2.01 min<br>(column J) |
| 41 | 6-MeOC(O)-naphthalen-2-yl | (R)-Me | 456.19 | 456.11<br>1.86 min<br>(column J) |

TABLE 3

Characterization of Compounds of Formula I with the Following Substructure:

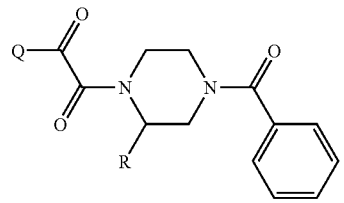

| Entry # | Q | R | MS (M + H)+ Calcd. | MS (M + H)+ Observ. And Retention Time |
|---|---|---|---|---|
| 1 | quinolin-2-yl | H | 374.15 | 374.07<br>1.27 min.<br>(Column A) |
| 5 | quinolin-2-yl | Me | 388.17 | 388.06<br>1.33 min.<br>(Column A) |
| 6 | quinolin-2-yl | (R)-Me | 388.17 | 388.10<br>1.33 min.<br>(Column A) |

TABLE 3-continued

Characterization of Compounds of Formula I with the Following Substructure:

| Entry # | Q | R | MS (M + H)+ Calcd. | MS (M + H)+ Observ. And Retention Time |
|---|---|---|---|---|
| 9 | quinolin-2-yl | (S)-Me | 388.17 | 388.10 1.34 min. (Column A) |
| 14 | quinoxalin-6-yl | H | 375.15 | 375.16 1.17 min. (Column A) |
| 2 | quinoxalin-2-yl | H | 375.15 | 375.08 1.18 min. (Column A) |
| 7 | quinoxalin-2-yl | (R)-Me | 389.16 | 389.09 1.24 min. (Column A) |
| 11 | quinoxalin-2-yl | (S)-Me | 389.16 | 389.09 1.24 min. (Column A) |
| 3 | isoquinolin-3-yl | H | 374.15 | 374.08 1.21 min. (Column A) |
| 8 | isoquinolin-3-yl | (R)-Me | 388.17 | 388.10 1.28 min. (Column A) |
| 12 | isoquinolin-3-yl | (S)-Me | 388.17 | 388.10 1.27 min. (Column A) |

TABLE 3-continued
Characterization of Compounds of Formula I with the Following Substructure:
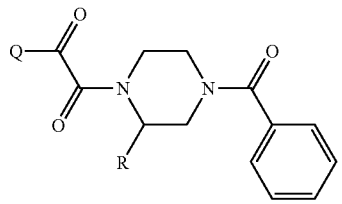
| Entry # | Q | R | MS (M + H)+ Calcd. | MS (M + H)+ Observ. And Retention Time |
|---|---|---|---|---|
| 4 | 2,6-naphthyridinyl | H | 375.15 | 375.13 0.96 min. (Column A) |
| 13 | 2,6-naphthyridinyl | (S)-Me | 389.16 | 389.08 1.03 min. (Column A) |
| 33 | 6-MeO-quinolinyl | Me | 418.18 | 418.26 1.45 min (column I) |
| 34 | 6-F-quinolinyl | Me | 406.16 | 406.09 1.39 min (column I) |
| 38 | 5-OMe-quinolinyl | Me | 418.18 | 418.21 1.51 min (column I) |
| 37 | 5-OH-quinolinyl | Me | 404.16 | 404.02 1.30 min (column I) |
| 35 | 6-Br-quinolinyl | Me | 466.08 | 465.81 1.66 min (column I) |

TABLE 3-continued
Characterization of Compounds of Formula I with the Following Substructure:
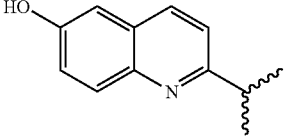
| Entry # | Q | R | MS (M + H)+ Calcd. | MS (M + H)+ Observ. And Retention Time |
|---|---|---|---|---|
| 36 | 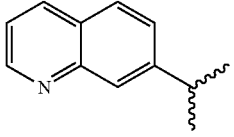 | Me | 404.16 | 403.95 1.41 min (column I) |
| 39 | 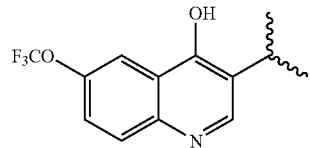 | H | 374.15 | 374.09 1.14 min (column I) |
| 28 | 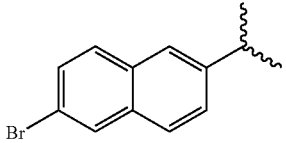 | Me | 488.14 | 488.00 1.58 min (column I) |
| 42 | 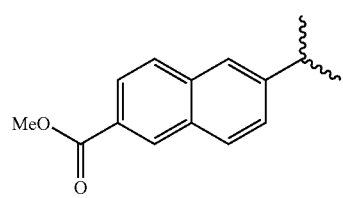 | (R)-Me | 465.08 | 466.97 1.81 min (column J) |
| 43 | 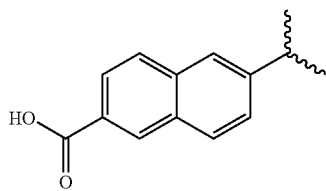 | (R)-Me | 445.18 | 445.08 1.67 min (column J) |
| 44 |  | (R)-Me | 431.16 | 431.06 1.55 min (column J) |

General Procedures in Scheme 4a:

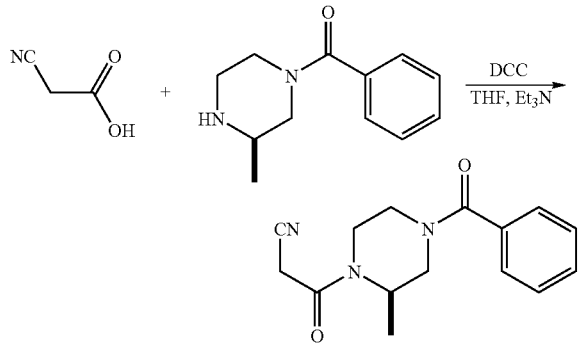

Preparation of (R)-N-benzoyl-N'-(2-cyano-acetyl)-2-methylpiperazine: DCC (2.43 g) and triethylamine (5 ml) were added into a solution of cyanoacetic acid (1 g) and (R)-N-benzoyl-N'-methylpiperazine (2.84 g) in THF (50 ml). After reaction stirred at room temperature for 12 hours, solvents were removed under vaccum to give a residue which was purified by silica gel column chromatography to afford 3 g of (R)-N-benzoyl-N'-(2-cyano-acetyl)-3-methylpiperazine. MS m/z: (M+H)$^+$ calcd for $C_{15}H_{18}N_3O_2$ 272.14, found 272.17. HPLC retention time: 0.93 minutes (column H).

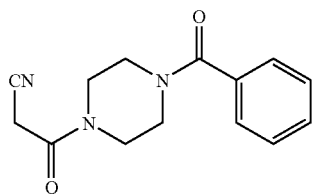

Preparation of N-benzoyl-N'-(2-cyano-acetyl)piperazine: N-benzoyl-N'-(2-cyano-acetyl)piperazine was prepared by the same method for of (R)-N-benzoyl-N'-(2-cyano-acetyl)-3-methylpiperazine. MS m/z: (M+H)$^+$ calcd for $C_{14}H_{16}N_3O_2$ 258.12, found 258.15. HPLC retention time: 0.83 minutes (column H).

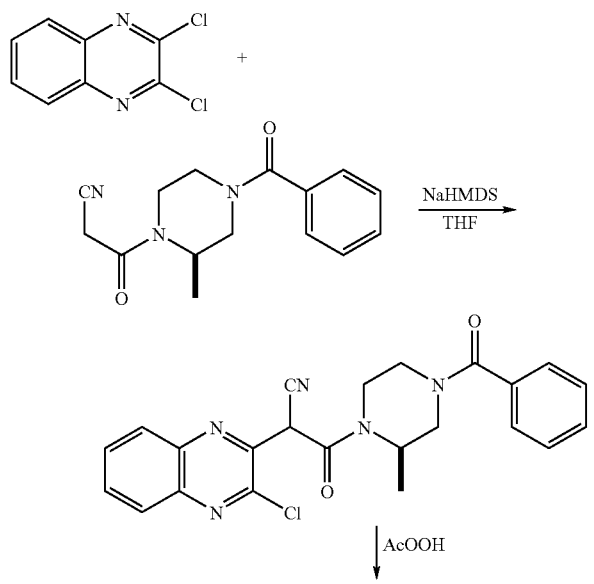

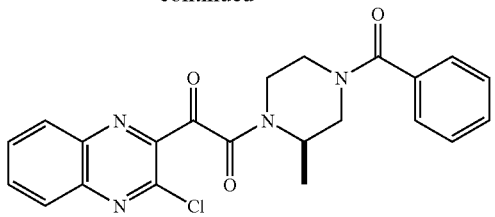

Typical procedure to prepare oxoacety-piperazines: Preparation of (R)-N-(benzoyl)-3-methyl-N'-[(3-chloro-quinoxalin-2-yl)-2-oxoacetyl]-piperazine: NaHMDS (1.53 ml, 1M in THF) was added into a solution of (R)-N-benzoyl-N'-(2-cyano-acetyl)-3-methylpiperazine (215 mg) and 2,3-dichloroquinoxaline (100 mg) in THF (10 ml). After the reaction was stirred for 10 hours, LC-MS showed the formation of (R)-N-(benzoyl)-3-methyl-N'-[(3-chloro-quinoxalin-2-yl)-2-cyanoacetyl]-piperazine, [MS m/z: (M+H)$^+$ calcd for $C_{23}H_{21}ClN_5O_2$ 434.14, found 434.12. HPLC retention time: 1.59 minutes (column H)]. Then, acetic peracid (4 ml, 25% in acetic acid) was added and the resulted mixture was stirred for another 1 hour to show the formation of (R)-N-(benzoyl)-3-methyl-N'-[(3-chloro-quinoxalin-2-yl)-2-oxoacetyl]-piperazine, [MS m/z: (M+H)$^+$ calcd for $C_{22}H_{20}ClN_4O_3$ 423.12, found 423.06. HPLC retention time: 1.67 minutes (column H)].

General Procedures in Scheme 4b:

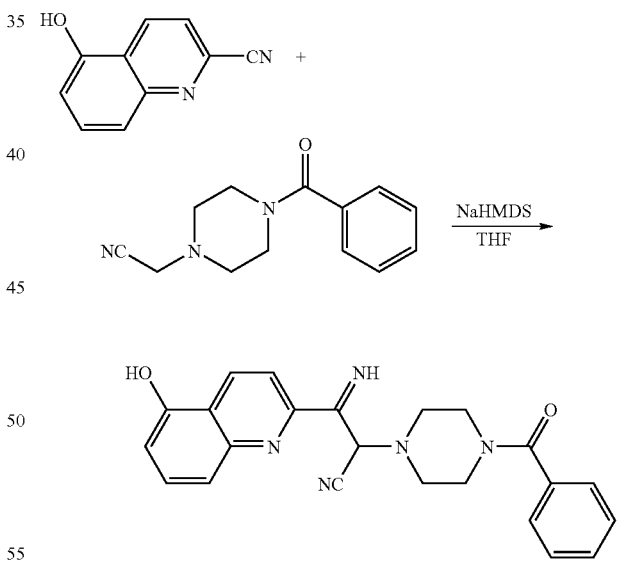

Typical procedure to prepare cyano-ketone: Preparation of N-(benzoyl)-N'-[2-(5-hydroxyl-quinolin-2-yl)-2-imino-1-cyano-ethyl]-piperazine: NaHMDS (1.75 ml, 1M in THF) was added into a solution of 1-benzyl-4-cyanomethylpiperazin (88.2 mg) and 2-cyano-5-hydroxylquinoline (62 mg) in THF. The reaction was stirred for 10 hours. After solvents were removed under vaccum, the residue was purified using Shimadzu automated preparative HPLC System to give N-(benzoyl)-N'-[2-(5-hydroxyl-quinolin-2-yl)-2-imino-1-cyano-ethyl]-piperazine (2.6 mg).

TABLE 4

Characterization of Compounds of Formula I with the Following Substructure:

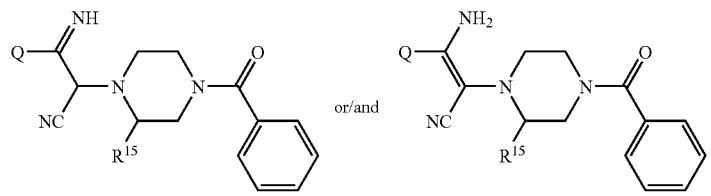

or/and

| Example | Q | $R^{15}$ | MS Cald. | MS Obsd. And Retention Time |
|---|---|---|---|---|
| 32 | 5-hydroxyquinolin-2-yl | Me | 414.19 | 413.96<br>1.40 min (column I) |
| 30 | 6-hydroxyquinolin-2-yl | Me | 414.19 | 414.15<br>1.30 min (column I) |
| 31 | 6-methoxyquinolin-2-yl | Me | 428.21 | 428.16<br>1.49 min (column I) |

Chemistry Experimental Section B

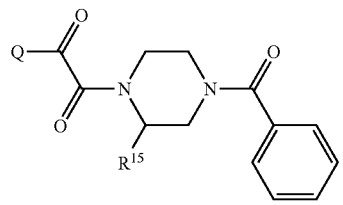

Indole Replacements

Scheme 10

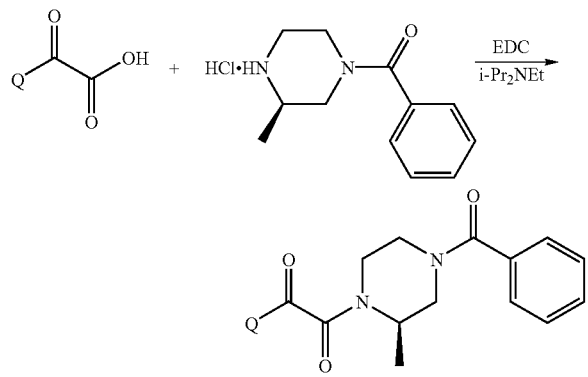

Some examples could be prepared by reaction of glyoxylic acid (QCOCOOH) with a piperidine or substituted piperidine hydrochloride in the presence of EDC (Scheme 10).

Example Preparation

To a solution of glyoxylic acid (QCOCOOH, 1 equiv.) in DMF was added (R)-methylbenzoyl piperazine hydrochloride (1.5 equiv), followed by EDC (1.5 equiv.) and I-Pr2NEt (3 equiv). The reaction mixture was stirred at room temperature for 16h and the crude product was purified by prep. HPLC. The compounds were characterized as shown above.

Scheme 11

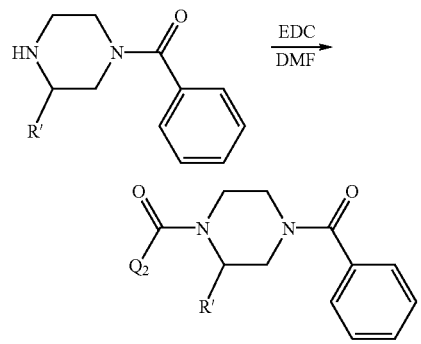

(Q₂ is Q—C(O)—⁣ for Table 3 and Q₂ is

Q—C(O)—CH(CN)—⁣ for Table 2 in Compounds of Formula I)

Examples 1–12 (Table 3) and Example 15–16 (Table 2) are prepared by reaction of commercially available carboxylic acids and benzoyl piperazine in the presence of EDC and catalytic 1-hydroxy-4-azabenzotriazole (Scheme 11).

Scheme 12

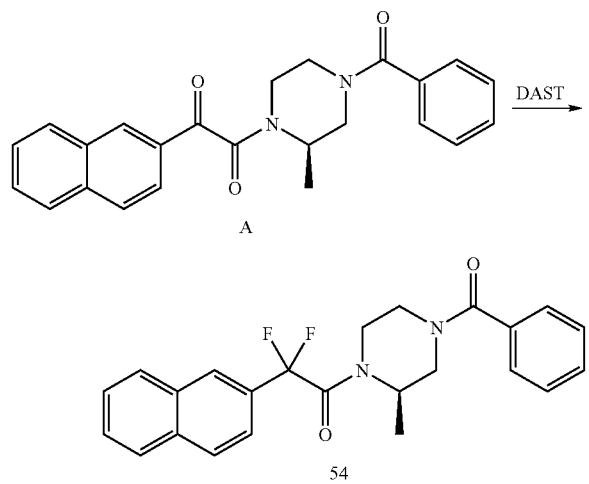

Example 54 (Table 8) is prepared by reaction of naphthalene glyoxamide A with neat DAST at 60° C. (Scheme 12).

Scheme 13

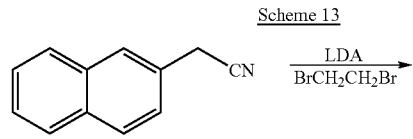

-continued

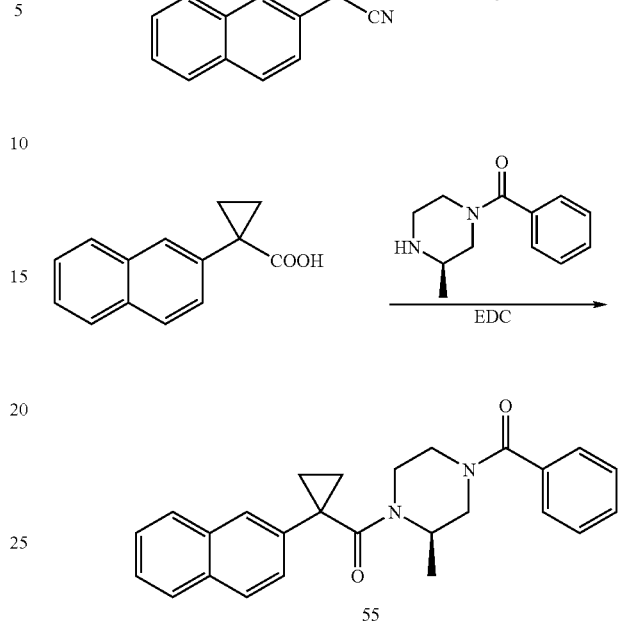

Example 55 is prepared in a three step procedure as shown in Scheme 13. Reaction of 2-napthylacetonitrile with LDA followed by quenching with 1,2-dibromoethane affords the desired α-cyclopropylnitrile. Hydrolysis then yields the corresponding acid which is then coupled with (R)-methylbenzoyl piperazine to afford the desired cyclopropyl derivative 55.

General Procedure for the Preparation of Examples 42–53 in Table 5

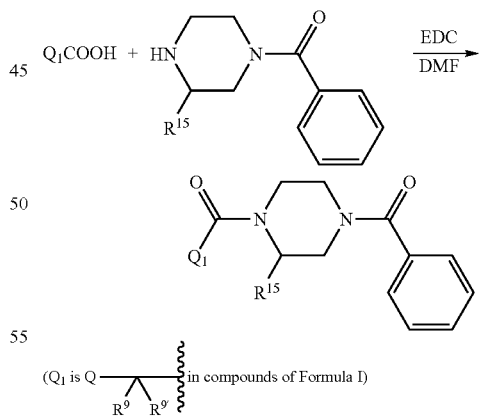

(Q₁ is Q—⁣ in compounds of Formula I)
    R⁹ R⁹

To commercially available carboxylic acid QCOOH (1 equiv.) in DMF was added benzoylpiperazine (1 equiv), 1-hydroxy-4-azabenzotriazole (0.2 equiv) followed by EDC (1 equiv) and i-Pr₂NEt (2 equiv). The reaction mixture was stirred at room temperature for 16 h. The crude products were then purified by prep HPLC and were characterized as shown in Table 5.

Procedure for the Preparation of Example 59

STEP A

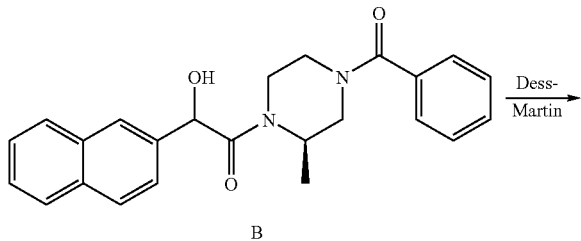

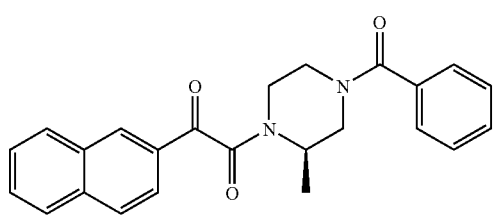

To α-hydroxyamide B (prepared as described above using commercially available naphthylglycolic acid) was added CH$_2$Cl$_2$ followed by Dess-Martin Periodinane (1.5 equiv.). The reaction mixture was stirred at room temperature for 4 h. The mixture was diluted with CH2Cl2 and was washed with water and brine, dried over MgSO4, filtered and concentrated. The crude product was purified by flash chromatography (0–50% EtOAc/Hexane) to yield the desired glyoxamide (HPLC retention time: 1.45 min. MS: 387 (M+H)$^+$).

STEP B

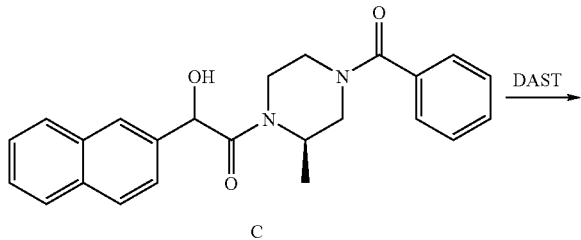

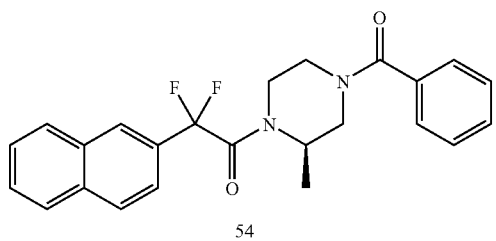

54

To the naphthalene glyoxamide C above (15 mg) was added DAST (250 uL). The reaction mixture was stirred at room temperature for 1 h and was then heated to 60° C. for 16 h. The reaction was quenched with MeOH and the crude product was purified by prep. HPLC to yield the desired α-difluoroamide.

Procedure for the Preparation of Example 55

STEP A

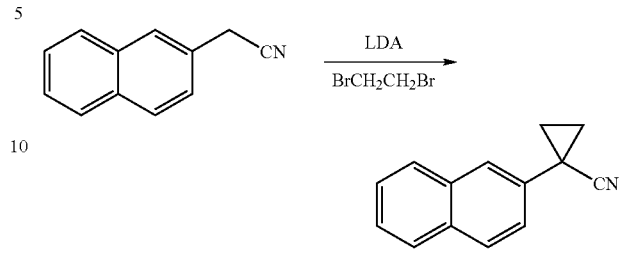

To 2-naphthylacetonitrile (167 mg, 1 mmol) in THF (5 mL) at −78° C. was added LDA (3.5 equiv). The reaction mixture was stirred for 30 min before the addition of 1,2-dibromoethane (375 mg, 2 equiv.). The mixture was then allowed to warm to room temperature and was stirred at rt for 16 h. The reaction was quenched with NH4Cl (aq) and was diluted with CH2Cl2. The organic phase was washed with water, 0.1 M HCl and brine, dried over MgSO4, filtered and concentrated. The product was then purified by flash chromatography (0–30% EtOAc/Hexane).

STEP B

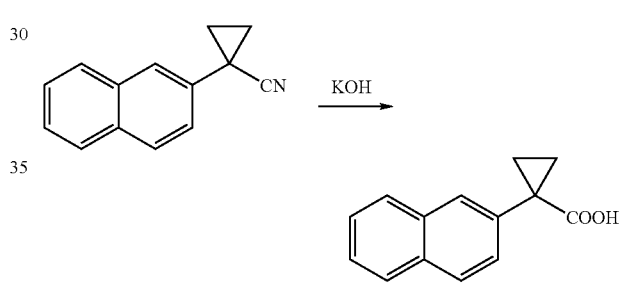

To cyclopropylamide shown above (70 mg) in EtOH/H2O (9:1, 10 mL) was added KOH (200 mg). The reaction mixture was then heated to reflux for 16 h. The reaction was then quenched with 1M HCl and the crude product was purified by prep. HPLC.

STEP C

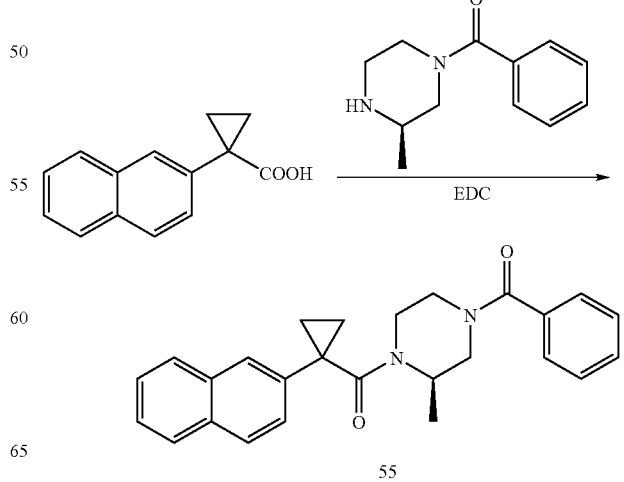

55

To cyclopropyl acid shown above (20 mg), (R)-methylpiperazine hydrochloride (27 mg) and EDC (28 mg) was added 1-hydroxy-7-azabenzotriazole (3 mg) followed by DMF (1 mL). The reaction mixture was stirred at room temperature for 16 h, and the crude product was purified by prep. HPLC.

TABLE 5

In Table 5, AZ means (Q-C(R9)(R9')-C(O)-) in compounds of Formula I.

| Example # | AZ | R15 | HPLC Retention Time | MS Data (M + H)+ |
|---|---|---|---|---|
| 42 | 1-naphthyl-CH2-C(O)- | H | 1.44 | 359 |
| 43 | 1-naphthyl-CH2-C(O)- | Me | 1.22 | 373 |
| 44 | 2-naphthyl-CH2-C(O)- | H | 1.48 | 359 |
| 45 | 2-naphthyl-CH2-C(O)- | Me | 1.23 | 373 |
| 46 | 2-naphthyl-CH(OH)-C(O)- | Me | 1.38 | 389 |
| 47 | 2-naphthyl-CH(OH)-C(O)- | Me | 1.38 | 389 |

TABLE 5-continued
In Table 5, AZ means 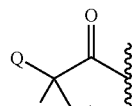 in compounds of Formula I.
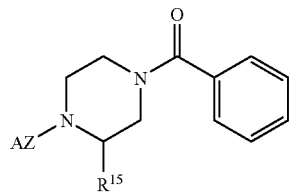
| Example # | AZ | R15 | HPLC Retention Time | MS Data (M + H)+ |
|---|---|---|---|---|
| 48 | 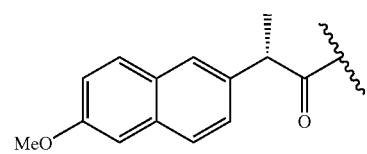 | (R)-Me | 1.56 | 417 |
| 49 | 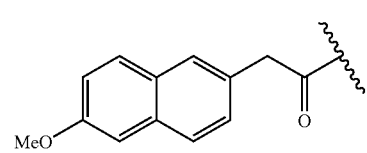 | H | 1.45 | 389 |
| 50 | 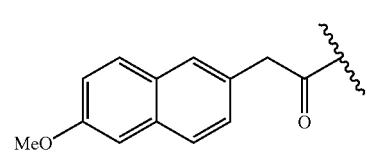 | (R)-Me | 1.44 | 403 |
| 51 | 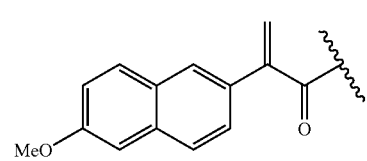 | H | 1.47 | 401 |
| 52 | 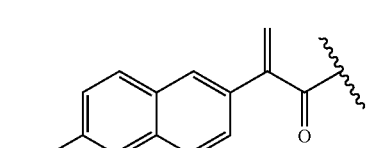 | (R)-Me | 1.52 | 415 |
| 53 | 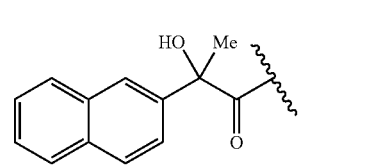 | (R)-Me | 1.59 | 403 |
| 54 | 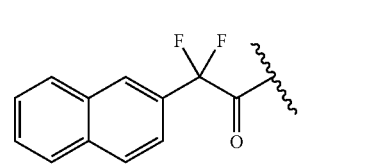 | (R)-Me | 1.62 | 409 |

TABLE 5-continued

In Table 5, AZ means [structure with R⁹, R⁹′, Q, O] in compounds of Formula I.

[structure: AZ–N-piperazine–C(O)–phenyl with R¹⁵]

| Example # | AZ | R¹⁵ | HPLC Retention Time | MS Data (M + H)⁺ |
|---|---|---|---|---|
| 55 | [2-naphthyl-cyclopropyl-C(O)] | (R)-Me | 1.67 | 399 |

Chemistry Experimental Section C

A Method for Preparing the Compounds of Formula I via Coupling of an Acetic Acid Derivative Followed by Appropriate Functionalization is Described.

Scheme 15

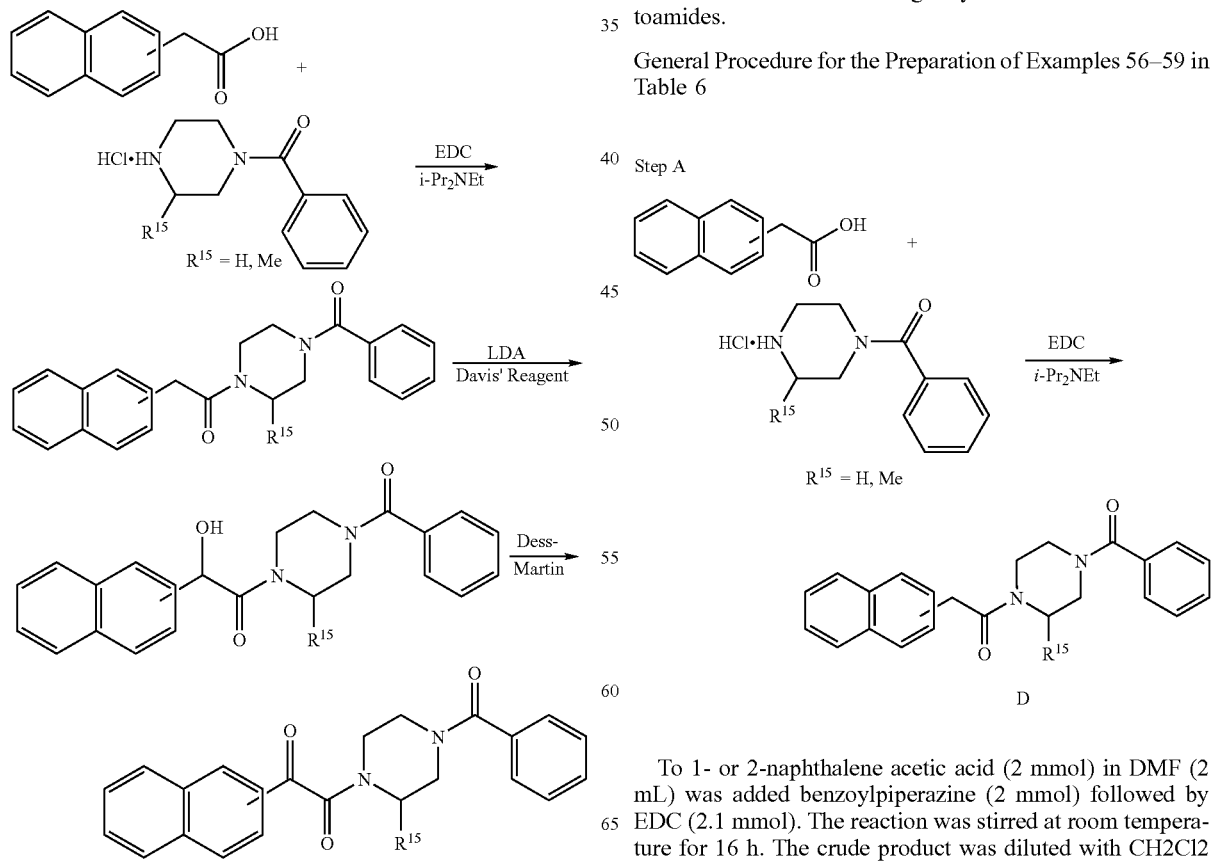

Examples 56–59 in (Table 6) were prepared in a three step procedure (Scheme 15). Reaction of commercially available 1- or 2-naphthalene acetic acid with benzoyl piperazine in the presence of EDC afforded the desired amides. Treatment with LDA followed by quenching with (+,−)-Davis' reagent afforded the corresponding α-hydroxyamides. Finally, oxidation with Dess-Martin reagent yielded the desired α-ketoamides.

General Procedure for the Preparation of Examples 56–59 in Table 6

Step A

To 1- or 2-naphthalene acetic acid (2 mmol) in DMF (2 mL) was added benzoylpiperazine (2 mmol) followed by EDC (2.1 mmol). The reaction was stirred at room temperature for 16 h. The crude product was diluted with CH2Cl2 and was washed with HCl (0.1 M), water and brine. The organic phase was dried over MgSO4, filtered and concentrated. The crude product was purified by flash chromatography (0–50% EtOAc/Hexane) to afford the desired amides.

Step B

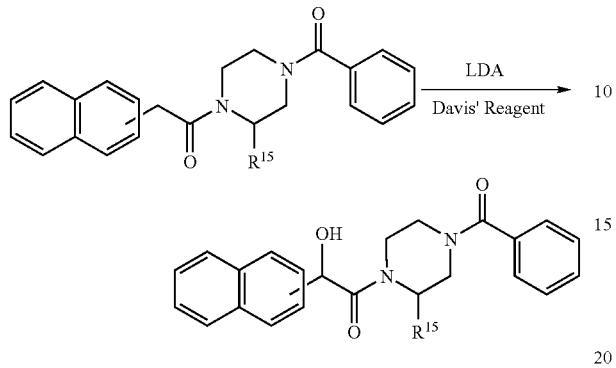

To naphthalene acetamide D prepared above (0.1 mmol) in THF (2 mL) was added (+,−)-Davis Reagent (0.1 mmol). The reaction mixture was cooled to −78° C. before LDA (200 uL, 1M in THF) was added. The mixture was stirred at −78° C. for 2 h and was then quenched with sat. NH4Cl. The solution was diluted with CH2Cl2 and was washed with 0.1M HCl, water and brine. The organic phase was dried over MgSO4, filtered and concentrated. The crude product was then purified by flash chromatography (0–60% EtOAc/Hexane) to afford the desire α-hydroxyamides.

Step C

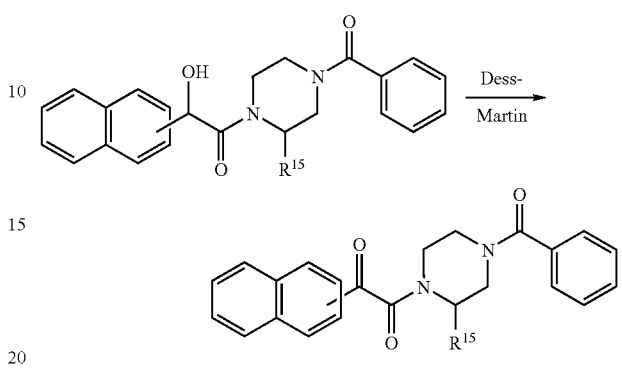

To α-hydroxyamide (1 equiv) in CH2Cl2 was added Dess-Martin Periodinane (2 equiv.). The reaction mixture was stirred at room temperature for 16 h and the crude product was then purified by prep. HPLC to afford the desired α-keto amide. The products were characterized as shown in Table 6.

TABLE 6

In Tables 6, 8 and 9, BZ is 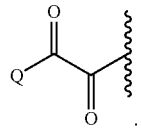

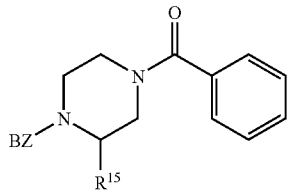

| Example # | BZ | R15 | HPLC Retention Time | MS Data (M + H)+ |
|---|---|---|---|---|
| 56 | [structure] | H | 1.54 | 373 |
| 57 | [structure] | H | 1.54 | 373 |

TABLE 6-continued

In Tables 6, 8 and 9, BZ is

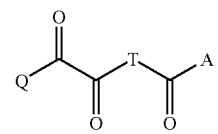

| Example # | BZ | R¹⁵ | HPLC Retention Time | MS Data (M + H)⁺ |
|---|---|---|---|---|
| 58 | | Me | 1.47 | 387 |
| 59 | | (R)-Me | 1.45 | 387 |

Preparation of Compounds of Formula I

General Procedure to Prepare Cyano-ketone Derivatives:

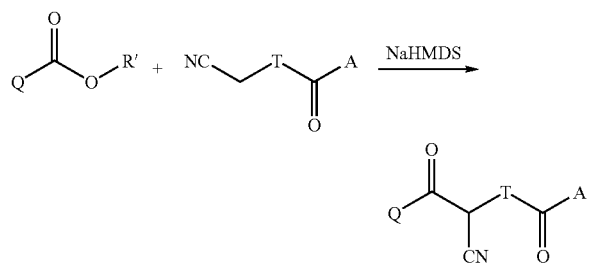

NaHMDS (1.75 mL, 1.0 M in THF) was added into a solution of an amido cyanomethylpiperazine derivative of formula AC(O)TCH₂CN (0.44 mmol) and carboxylate of formula QC(O)OR' (R' is methyl or ethyl, 0.44 mmol) in THF. The reaction was stirred for 10 hours at room temperature then was concentrated in vacuo. The residue was purified using Shimadzu automated preparative HPLC System to give the product of general formula QC(O)CH(CN)TC(O)A.

General Procedure to Prepare Oxoacetylpiperazine Derivatives:

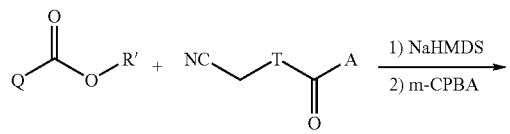

-continued

General procedure to prepare oxoacetyl-piperazines: NaHMDS (1.75 mL, 1.0 M in THF) was added into a solution of an appropriate cyanomethylpiperazine derivative of formula AC(O)TCH₂CN, (0.44 mmol), and an appropriate heterocyclic carboxylate of formula QCO₂R', where R' is methyl or ethyl, (0.44 mmol) in an appropriate solvent such as THF. After the reaction was stirred for 10 hours at room temperature, mCPBA (200 mg, >77%) was added and the resulting mixture was stirred for another 10 hours at room temperature. Then the reaction mixture was concentrated in vacuo and the residue was purified using Shimadzu automated preparative HPLC System or by column chromatography or thin layer chromatography to provide the oxoacetylpiperazine derivative of formula QC(O)C(O)TC(O)A.

Biology

In Tables 7–9 and hereafter, the following definitions apply.
"μM" means micromolar;
"ml" means milliliter;
"μl" means microliter;
"mg" means milligram;

The materials and experimental procedures used to obtain the results for representative compounds of Formula I reported in Tables 7–9 are described below.

87

Cells:
Virus production—Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).
Virus infection—Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis, Mo.) and supplemented with 0.2 mg/ml Geneticin (Life Technologies, Gaithersburg, Md.) and 0.4 mg/ml Zeocin (Invitrogen, Carlsbad, Calif.).
Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Life Technologies, Gaithersburg, Md.).

Experiment
1. Compound was added to HeLa CD4 CCR5 cells plated in 96 well plates at a cell density of $5 \times 10^4$ cells per well in 100 µl Dulbecco's Modified Eagle Medium containing 10% fetal Bovine serum at a concentration of <20 µM.
2. 100 µl of single-round infectious reporter virus in Dulbecco's Modified Eagle Medium was then added to the plated cells and compound at an approximate multiplicity of infection (MOI) of 0.01, resulting in a final volume of 200 µl per well and a final compound concentration of <10 µM.
3. Samples were harvested 72 hours after infection.
4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 µl of Dulbecco's Modified Eagle Medium (without phenol red) and 50 µl of luciferase assay reagent reconstituted as described by the manufacturer (Roche Molecular Biochemicals, Indianapolis, Ind.) was added per well. Luciferase activity was then quantified by measuring luminescence using a Wallac microbeta scintillation counter.
5. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data obtained is shown below in Tables 7–9. In Tables 7–9, compounds with an $EC_{50}$ of greater than 5 µM are designated as Group C; compounds with an $EC_{50}$ of 1 µM to 5 µM are designated Group B; compounds with an $EC_{50}$ of less than 1 µM are designated as Group A; and compounds with a potency of greater than 0.5 µM which were not evaluated at higher doses to determine the $EC_{50}$ value are designated Group D.

TABLE 7

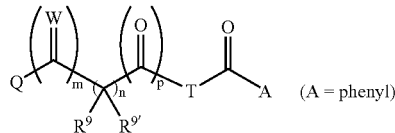

I   (A = phenyl)

| Example # | Q | W, m, n, p, $R^9$, $R^{9'}$ | T | Group |
|---|---|---|---|---|
| 1 | quinolin-2-yl | m = 1, n = 0, p = 1 | piperazine | A |
| 2 | quinoxalin-2-yl | m = 1, n = 0, p = 1 | piperazine | A |
| 3 | isoquinolin-3-yl | m = 1, n = 0, p = 1 | piperazine | A |

TABLE 7-continued

I (structure: Q-(W)m-C(=O)-(CR9R9')n-C(=O)p-T-C(=O)-A, A = phenyl)

| Example # | Q | W, m, n, p, R9, R9' | T | Group |
|---|---|---|---|---|
| 4 | 1,6-naphthyridin-2-yl | m = 1, n = 0, p = 1 | piperazine | A |
| 5 | quinolin-2-yl | m = 1, n = 0, p = 1 | (2-methyl)piperazine (H3C, H) | A |
| 6 | quinolin-2-yl | m = 1, n = 0, p = 1 | 3-methylpiperazine | A |
| 7 | quinoxalin-2-yl | m = 1, n = 0, p = 1 | piperazine | A |
| 8 | isoquinolin-3-yl | m = 1, n = 0, p = 1 | (R or S)-3-methylpiperazine | A |
| 9 | quinolin-2-yl | m = 1, n = 0, p = 1 | 3-methylpiperazine (wedge) | A |
| 11 | quinoxalin-2-yl | m = 1, n = 0, p = 1 | 3-methylpiperazine (wedge) | A |
| 12 | isoquinolin-3-yl | m = 1, n = 0, p = 1 | 3-methylpiperazine | A |
| 13 | 1,6-naphthyridin-2-yl | m = 1, n = 0, p = 1 | 3-methylpiperazine (dashed) | A |

TABLE 7-continued

Structure I: Q-(W)ₘ-(CR⁹R⁹')ₙ-(C(O))ₚ-T-C(O)-A (A = phenyl)

| Example # | Q | W, m, n, p, R⁹, R⁹' | T | Group |
|---|---|---|---|---|
| 14 | quinoxalin-2-yl | m = 1, n = 0, p = 1 | piperazine | B |
| 15 | quinolin-2-yl | m = 1, n = 1, p = 0, R⁹ = —CN, R⁹' = —H | 2-methylpiperazine (H₃C, H) | A |
| 16 | quinolin-2-yl | m = 1, n = 1, p = 0, R⁹ = —CN, R⁹' = —H | piperazine | A |
| 17 | isoquinolin-3-yl | m = 1, n = 1, p = 0, R⁹ = —CN, R⁹' = —H | piperazine | A |
| 18 | quinolin-2-yl | m = 1, n = 1, p = 0, R⁹ = —CN, R⁹' = —H | 3-methylpiperazine (H₃C down) | A |
| 19 | quinoxalin-2-yl | m = 1, n = 1, p = 0, R⁹ = —CN, R⁹' = —H | 3-methylpiperazine (H₃C down) | A |
| 20 | 1,6-naphthyridin-2-yl | m = 1, n = 1, p = 0, R⁹ = —CN, R⁹' = —H | 3-methylpiperazine (H₃C down) | B |
| 21 | quinolin-2-yl | m = 1, n = 1, p = 0, R⁹ = —CN, R⁹' = —H | 3-methylpiperazine (H₃C wedge) | A |
| 22 | 1,6-naphthyridin-2-yl | m = 1, n = 1, p = 0, R⁹ = —CN, R⁹' = —H | 3-methylpiperazine (H₃C wedge) | B |

TABLE 7-continued

I (structure: Q-(W)-[C(=O)]m-C(R9)(R9')-[C(=O)]n-(T)p-C(=O)-A, A = phenyl)

| Example # | Q | W, m, n, p, R9, R9' | T | Group |
|---|---|---|---|---|
| 23 | quinoxalin-2-yl | m = 1, n = 1, p = 0, R9 = —CN, R9' = —H | (S)-2-methylpiperazine | B |
| 24 | 5,8-difluoro-4-(phenylthio)quinolin-3-yl | m = 1, n = 1, p = 0, R9 = —CN, R9' = —H | piperazine | B |
| 25 | 6-bromoquinolin-2-yl | m = 1, n = 1, p = 0, R9 = —CN, R9' = —H | (2S)-2-methylpiperazine | A |
| 26 | 6-hydroxyquinolin-2-yl | m = 1, n = 1, p = 0, R9 = —CN, R9' = —H | (2S)-2-methylpiperazine | A |
| 27 | 4-hydroxy-6-(trifluoromethoxy)quinolin-3-yl | m = 1, n = 1, p = 0, R9 = —CN, R9' = —H | (2S)-2-methylpiperazine | A |
| 28 | 4-hydroxy-6-(trifluoromethoxy)quinolin-3-yl | m = 1, n = 0, p = 1 | (2S)-2-methylpiperazine | D |
| 29 | 6-methoxyquinolin-2-yl | m = 1, n = 1, p = 0, R9 = —CN, R9' = —H | (2S)-2-methylpiperazine | A |
| 30 | 6-hydroxyquinolin-2-yl | W = NH, m = 1, n = 1, p = 0, R9 = —CN, R9' = —H | (2S)-2-methylpiperazine | D |

TABLE 7-continued

Structure I: Q-(W)ₘ-C(R⁹)(R⁹')-(C=O)ₙ-(...)ₚ-T-C(=O)-A  (A = phenyl)

| Example # | Q | W, m, n, p, R⁹, R⁹' | T | Group |
|---|---|---|---|---|
| 31 | 6-MeO-quinolin-2-yl | W = NH, m = 1, n = 1, p = 0, R⁹ = —CN, R⁹' = —H | 2-methylpiperazinyl | D |
| 32 | 5-OH-quinolin-2-yl | W = NH, m = 1, n = 1, p = 0, R⁹ = —CN, R⁹' = —H | 2-methylpiperazinyl | A |
| 33 | 6-MeO-quinolin-2-yl | m = 1, n = 0, p = 1 | 2-methylpiperazinyl | A |
| 34 | 6-F-quinolin-2-yl | m = 1, n = 0, p = 1 | 2-methylpiperazinyl | A |
| 35 | 6-Br-quinolin-2-yl | m = 1, n = 0, p = 1 | 2-methylpiperazinyl | A |
| 36 | 6-HO-quinolin-2-yl | m = 1, n = 0, p = 1 | 2-methylpiperazinyl | A |
| 37 | 5-OH-quinolin-2-yl | m = 1, n = 0, p = 1 | 2-methylpiperazinyl | A |
| 38 | 5-OMe-quinolin-2-yl | m = 1, n = 0, p = 1 | 2-methylpiperazinyl | A |

TABLE 7-continued

Structure I: Q-(W)m-C(R9)(R9')-(n)-C(=O)p-T-C(=O)-A  (A = phenyl)

| Example # | Q | W, m, n, p, R9, R9' | T | Group |
|---|---|---|---|---|
| 39 | quinolin-7-yl | m = 1, n = 0, p = 1 | piperazine | B |
| 40 | 1,6-naphthyridin-2-yl | m = 1, n = 1, p = 0, R9 = —CN, R9' = —H | piperazine | C |
| 41 | quinoxalin-2-yl | m = 1, n = 0, p = 1 | piperazine | B |
| 44 | 6-(HO2C)-naphthalen-2-yl | m = 1, n = 0, p = 1 | (3S)-3-methylpiperazine | A |

W = O unless indicated

TABLE 8

Structure: BZ—N(piperazine with R15)—C(=O)—phenyl

| Example # | BZ | R15 | Group |
|---|---|---|---|
| 42 | 1-naphthyl-CH2-C(=O)- | H | B |

TABLE 8-continued
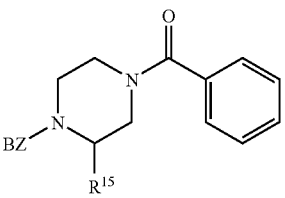
| Example # | BZ | R15 | Group |
|---|---|---|---|
| 43 | 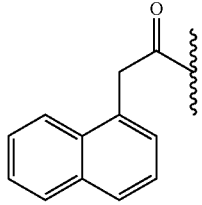 | Me | B |
| 44 | 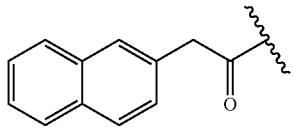 | H | B |
| 45 | 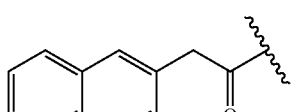 | Me | B |
| 46 | 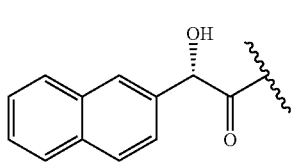 | Me | B |
| 47 | 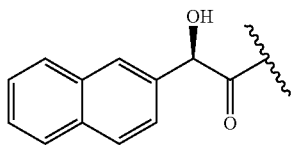 | Me | B |
| 48 | 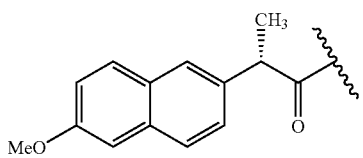 | (R)-Me | B |
| 49 | 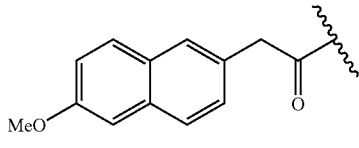 | H | A |
| 50 | 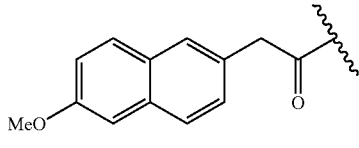 | (R)-Me | A |

TABLE 8-continued
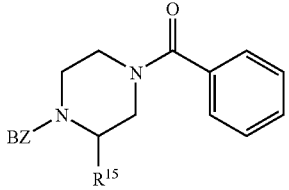
| Example # | BZ | R15 | Group |
|---|---|---|---|
| 51 | 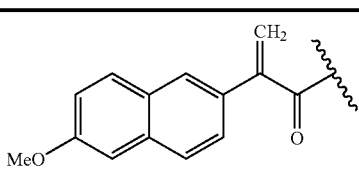 6-methoxynaphthalen-2-yl with CH2 and C=O | H | A |
| 52 | 6-methoxynaphthalen-2-yl with CH2 and C=O | (R)-Me | A |
| 53 | naphthalen-2-yl with C(OH)(Me) and C=O | (R)-Me | B |
| 54 | naphthalen-2-yl with CF2 and C=O | (R)-Me | A |
| 55 | naphthalen-2-yl with cyclopropyl and C=O | (R)-Me | A |
TABLE 9
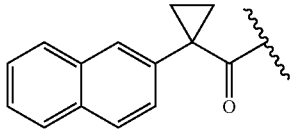
| Example # | BZ | R15 | Group |
|---|---|---|---|
| 56 | 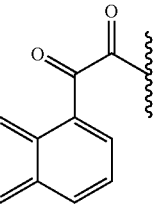 naphthalen-1-yl-C(O)-C(O)- | H | A |
| 57 | naphthalen-2-yl-C(O)-C(O)- | H | A |

TABLE 9-continued

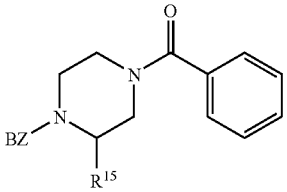

| Example # | BZ | R15 | Group |
|---|---|---|---|
| 58 | 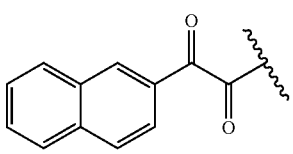 | Me | A |
| 59 | 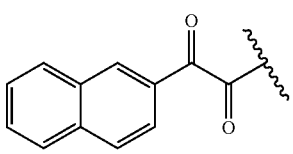 | (R)-Me | A |

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present invention.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound of Formula I, including pharmaceutically acceptable salts thereof,

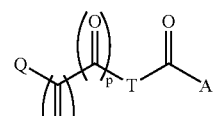

wherein: Q is 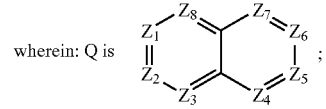 ;

A is phenyl or heteroaryl; wherein said heteroaryl is a monocyclic ring and is comprised of 5 to 6 atoms selected from the group consisting of C, N, NR$^9$, O, and S; and wherein each ring of said phenyl and heteroaryl is optionally substituted with one bromo, fluoro, or methyl group;

W is O;

T is

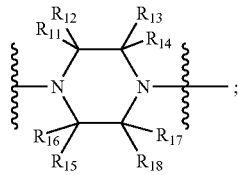

$Z^1$ is $CR^1$ or N;
$Z^2$ is $CR^2$ or N;
$Z^3$ is $CR^3$ or N;
$Z^4$ is $CR^4$ or N;
$Z^5$ is $CR^5$ or N;
$Z^6$ is $CR^6$ or N;
$Z^7$ is $CR^7$ or N;
$Z^8$ is $CR^8$ or N;
wherein one and not more than one of $Z^1$ through $Z^8$ is N;
$R^1$, $R^2$, $R^3$, $R^4$, $R^5$, $R^6$, $R^7$ and $R^8$ are each independently selected from the group consisting of a bond, hydrogen, halogen, cyano, nitro, X'R$^{24}$, C$_{1-6}$alkyl, C$_{3-7}$cycloalkyl, C$_{2-6}$alkenyl, C$_{4-7}$cycloalkenyl, C$_{2-6}$alkynyl, aryl, heteroaryl, heteroalicyclic, C(O)NR$^{28}$R$^{29}$, COR$^{25}$ and CO$_2$R$^{25}$; wherein said C$_{1-6}$alkyl, C$_{3-7}$cycloalkyl, C$_{2-6}$alkenyl, C$_{4-7}$cycloalkenyl, C$_{2-6}$alkynyl, aryl, heteroaryl, and heteroalicyclic are optionally substituted with one to nine same or different halogens or from one to five same or different substituents selected from the substituents comprising group F;

m is 1; p is 1;

F is selected from the group consisting of C$_{1-6}$alkyl, hydroxy, C$_{1-6}$alkoxy, cyano, halogen, benzyl, N-amido, NR$^{30}$R$^{31}$, C$_{1-6}$alkylC(O)NR$^{30}$R$^{31}$, C(O)NR$^{30}$R$^{31}$, COOR$^{32}$ and C$_{1-6}$alkylCOOR$^{32}$;

$R^9$ is selected from the group consisting of hydrogen, hydroxy, $C_{1-6}$alkyl, $C_{1-6}$alkoxy, cyano, and fluoro;

$R^{11}$, $R^{12}$, $R^{13}$, $R^{14}$, $R^{15}$, $R^{16}$, $R^{17}$ and $R^{18}$ are each independently selected from the group consisting of hydrogen and methyl;

X' is selected from the group consisting of $NR^{10}$, O, and S;

$R^{24}$ is hydrogen or $C_{1-6}$alkyl;

$R^{25}$ is selected from the group consisting of hydrogen, $C_{1-6}$alkyl, $C_{3-7}$cycloalkyl, aryl and heteroaryl;

$R^{28}$ and $R^{29}$ are each independently selected from the group consisting of hydrogen, $SO_2C_{1-6}$alkyl, $C_{1-6}$alkyl, $C_{3-7}$cycloalkyl, aryl, heteroaryl, and heteroalicyclic wherein said $C_{1-6}$alkyl, $C_{3-7}$cycloalkyl, aryl, heteroaryl, and heteroalicyclic are optionally substituted with one to nine same or different halogens or $C_{1-6}$alkyl groups;

$R^{30}$ and $R^{31}$ are each independently selected from the group consisting of hydrogen, $C_{1-6}$alkyl, $C_{3-7}$cycloalkyl, aryl, wherein said $C_{1-6}$alkyl, $C_{3-7}$cycloalkyl, and aryl are optionally substituted with one to nine same or different halogens;

$R^{32}$ is selected from the group consisting of hydrogen, $C_{1-6}$alkyl, and $C_{3-7}$cycloalkyl;

provided that at any given time only one of the members selected from the group consisting of $R^1$, $R^2$, $R^3$, $R^4$, $R^5$, $R^6$, $R^7$ and $R^8$ is a bond, and further provided that said bond is the point of attachment to the adjacent carbon atom in the compound of Formula I.

2. A compound of claim 1, including pharmaceutically acceptable salts thereof, wherein:

Q is:

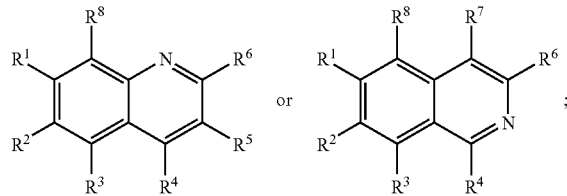

and $R^6$ is a bond for point of attachment.

3. A compound of claim 2, including pharmaceutically acceptable salts thereof, wherein:

Q is

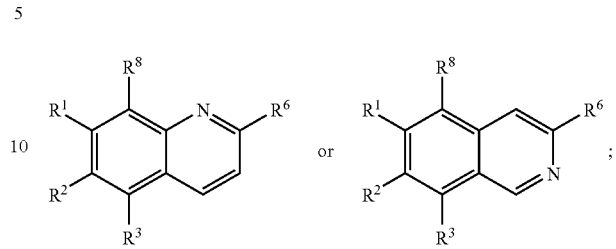

and $R^5$ is a bond for point of attachment.

4. A compound of claim 2, including pharmaceutically acceptable salts thereof, wherein:

Q is

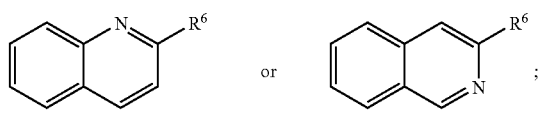

and $R^6$ is a bond for point of attachment.

5. A pharmaceutical composition which comprises an antiviral effective amount of a compound of Formula I, including pharmaceutically acceptable salts thereof, as claimed in claim 1, and on or more pharmaceutically acceptable carriers, excipients or diluents.

6. A method for treating a mammal infected with HIV, comprising administering to said mammal an antiviral effective amount of a compound of Formula I, including pharmaceutically acceptable salts thereof, as claimed in claim 1, and one or more pharmaceutically acceptable carriers, excipients or diluents.

* * * * *